(12) United States Patent
Mihara et al.

(10) Patent No.: US 9,279,109 B2
(45) Date of Patent: Mar. 8, 2016

(54) METHOD FOR PRODUCTION OF RECOMBINANT HUMAN IDURONATE 2-SULFATASE

(75) Inventors: Kazutoshi Mihara, Hyogo (JP); Atsuko Kawasaki, Hyogo (JP); Kouta Ootsuki, Hyogo (JP); Yuukichi Hatano, Hyogo (JP); Shoichiro Kamei, Hyogo (JP); Atsushi Sugimura, Hyogo (JP)

(73) Assignee: JCR Pharmaceuticals Co., Ltd., Ashiya-shi (JP)

( * ) Notice: Subject to any disclaimer, the term of this patent is extended or adjusted under 35 U.S.C. 154(b) by 0 days.

(21) Appl. No.: 13/979,973

(22) PCT Filed: Jan. 23, 2012

(86) PCT No.: PCT/JP2012/000365
§ 371 (c)(1),
(2), (4) Date: Aug. 7, 2013

(87) PCT Pub. No.: WO2012/101998
PCT Pub. Date: Aug. 2, 2012

(65) Prior Publication Data
US 2013/0330802 A1     Dec. 12, 2013

(30) Foreign Application Priority Data

Jan. 25, 2011   (JP) .................... PCT/JP2011/000392

(51) Int. Cl.
*C12N 9/16* (2006.01)

(52) U.S. Cl.
CPC ........... *C12N 9/16* (2013.01); *C12Y 301/06013* (2013.01)

(58) Field of Classification Search
CPC .......................... C12N 9/16; C12Y 301/06013
USPC .................................................. 435/188, 196
See application file for complete search history.

(56) References Cited

U.S. PATENT DOCUMENTS

| | | | |
|---|---|---|---|
| 5,932,211 A | 8/1999 | Wilson et al. | |
| 2009/0291473 A1 | 11/2009 | Sugimura et al. | |
| 2011/0105734 A1 | 5/2011 | Kawasaki et al. | |

FOREIGN PATENT DOCUMENTS

| JP | 2009-273427 | 11/2009 |
|---|---|---|
| JP | 2010-511378 | 4/2010 |

OTHER PUBLICATIONS

Muenzer et al., Genetics in Medicine 8(8) 465-473 (2006).*
Wilson et al., "Hunter syndrome: Isolation of an iduronate-2-sulfatase cDNA clone and analysis of patient DNA," Proc. Natl. Acad. Sci., 1990, vol. 87, pp. 8531-8535.
Dean et al., "Enzyme replacement therapy by fibroblast transplantation. Long-term biochemical study in three cases of Hunter's syndrome," J. Clin. Invest., 1979, vol. 63, pp. 138-145.
Brown et al., "Administration of iduronate sulfatase by plasma exchange to patients with the Hunter syndrome: a clinical study," Am J Med Genet, 1982, 13, pp. 309-318.
Wasteson et al., "Iduronate sulfatase from human plasma," Methods in Enzymology, 1982, vol. 83, pp. 573-578.
Natale et al., "Iduronate sulfatase from human placenta," Biochimica Biophysica Acta, 1985, vol. 839, No. 3, pp. 258-261.
Bielicki et al., "Recombinant human iduronate-2-sulphatase: correction of mucopolysaccharidosis-type II fibroblasts and characterization of the purified enzyme," Biochem J., 1993, vol. 289, No. 1, pp. 241-246.
Yutaka et al., "Purification and some properties of human liver iduronate sulfatase," J Biochem, 1982, vol. 91, No. 2, pp. 433-441.
Bielicki et al., "Human liver iduronate-2-sulphatase," Biochem J, 1990, vol. 271, No. 1, pp. 75-86.

\* cited by examiner

*Primary Examiner* — Nashaat Nashed
(74) *Attorney, Agent, or Firm* — Hamre, Schumann, Mueller & Larson, P.C.

(57) ABSTRACT

Disclosed is a method for production of recombinant human iduronate 2-sulfatase (rhI2S) (the 26th to 550th amino acids of SEQ ID NO: 10) in a large scale, with a high purity, and mannose 6-phosphate residues. The method comprises the steps of (a) culturing rhI2S (the 26th to 550th amino acids of SEQ ID NO: 10)-producing mammalian cells in a serum-free medium, (b) collecting culture supernatant, (c) subjecting the culture supernatant to cation-exchange column chromatography, (d) to dye affinity column chromatography, (e) to anion-exchange column chromatography, and (f) to a column chromatography employing as solid phase a material having affinity for phosphate group, and (g) to gel filtration column chromatography, in the order.

8 Claims, 8 Drawing Sheets

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Primer I2S-f, synthetic sequence

<400> SEQUENCE: 1
acgcctattg ctgcaggatg                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer I2S-r, synthetic sequence

<400> SEQUENCE: 2
aaacgaccag ctctaactcc                                                     20

<210> SEQ ID NO 3
<211> LENGTH: 30
<212> TYPE: DNA
<213> ORGANISM: Artificial Sequence
<220> FEATURE:
<223> OTHER INFORMATION: Primer I2S-f2, synthetic sequence

<400> SEQUENCE: 3
atactcgagg ccaccatgcc gccaccccgg                                          30

<210> SEQ ID NO 4
<211> LENGTH: 30
<212> TYPE: DNA
<213> ORGANISM: Artificial Sequence
<220> FEATURE:
<223> OTHER INFORMATION: Primer I2S-r2, synthetic sequence

<400> SEQUENCE: 4
ttcttatgcg gccgctcaag gcatcaacaa                                          30

<210> SEQ ID NO 5
<211> LENGTH: 101
<212> TYPE: DNA
```

```
<213> ORGANISM: Artificial Sequence
<220> FEATURE:
<223> OTHER INFORMATION: hGH-f1, synthetic sequence

<400> SEQUENCE: 5
ggccgctcta gacccgggtg gcatccctgt gaccccctccc cagtgcctct cctggccctg     60
gaagttgcca ctccagtgcc caccagcctt gtcctaataa a                        101

<210> SEQ ID NO 6
<211> LENGTH: 111
<212> TYPE: DNA
<213> ORGANISM: Artificial Sequence
<220> FEATURE:
<223> OTHER INFORMATION: hGH-r1, synthetic sequence

<400> SEQUENCE: 6
tgatgcaact taattttatt aggacaaggc tggtgggcac tggagtggca acttccaggg     60
ccaggagagg cactggggag gggtcacagg gatgccaccc gggtctagag c             111

<210> SEQ ID NO 7
<211> LENGTH: 96
<212> TYPE: DNA
<213> ORGANISM: Artificial Sequence
<220> FEATURE:
<223> OTHER INFORMATION: hGH-f2, synthetic sequence

<400> SEQUENCE: 7
attaagttgc atcatttgt ctgactaggt gtccttctat aatagcgcag caccatggcc      60
tgaaataacc tctgaaagag gaacttggtt aggtac                               96

<210> SEQ ID NO 8
<211> LENGTH: 78
<212> TYPE: DNA
<213> ORGANISM: Artificial Sequence
<220> FEATURE:
<223> OTHER INFORMATION: hGH-r2, synthetic sequence

<400> SEQUENCE: 8
ctaaccaagt tcctctttca gaggttattt caggccatgg tgctgcgcta ttatagaagg     60
acacctagtc agacaaaa                                                   78

<210> SEQ ID NO 9
<211> LENGTH: 1653
<212> TYPE: DNA
<213> ORGANISM: Homo sapiens
<220> FEATURE:
<221> NAME/KEY: CDS
<222> LOCATION: (1)..(1653)

<400> SEQUENCE: 9 atg ccg cca ccc cgg acc ggc cga ggc ctt ctc tgg ctg ggt ctg gtt       48
Met Pro Pro Pro Arg Thr Gly Arg Gly Leu Leu Trp Leu Gly Leu Val
1               5                   10                  15 ctg agc tcc gtc tgc gtc gcc ctc gga tcc gaa acg cag gcc aac tcg        96
Leu Ser Ser Val Cys Val Ala Leu Gly Ser Glu Thr Gln Ala Asn Ser
            20                  25                  30 acc aca gat gct ctg aac gtt ctt ctc atc atc gtg gat gac ctg cgc       144
Thr Thr Asp Ala Leu Asn Val Leu Leu Ile Ile Val Asp Asp Leu Arg
        35                  40                  45 ccc tcc ctg ggc tgt tat ggg gat aag ctg gtg agg tcc cca aat att       192
Pro Ser Leu Gly Cys Tyr Gly Asp Lys Leu Val Arg Ser Pro Asn Ile
    50                  55                  60
```

```
                                          -continued gac caa ctg gca tcc cac agc ctc ctc ttc cag aat gcc ttt gcg cag    240
Asp Gln Leu Ala Ser His Ser Leu Leu Phe Gln Asn Ala Phe Ala Gln
 65                  70                  75                  80 caa gca gtg tgc gcc ccg agc cgc gtt tct ttc ctc act ggc agg aga    288
Gln Ala Val Cys Ala Pro Ser Arg Val Ser Phe Leu Thr Gly Arg Arg
                 85                  90                  95 cct gac acc acc cgc tac gac ttc aac tcc tac tgg agg gtg cac        336
Pro Asp Thr Thr Arg Leu Tyr Asp Phe Asn Ser Tyr Trp Arg Val His
            100                 105                 110 gct gga aac ttc tcc acc atc ccc cag tac ttc aag gag aat ggc tat    384
Ala Gly Asn Phe Ser Thr Ile Pro Gln Tyr Phe Lys Glu Asn Gly Tyr
        115                 120                 125 gtg acc atg tcg gtg gga aaa gtc ttt cac cct ggg ata tct tct aac    432
Val Thr Met Ser Val Gly Lys Val Phe His Pro Gly Ile Ser Ser Asn
    130                 135                 140 cat acc gat gat tct ccg tat agc tgg tct ttt cca cct tat cat cct    480
His Thr Asp Asp Ser Pro Tyr Ser Trp Ser Phe Pro Pro Tyr His Pro
145                 150                 155                 160 tcc tct gag aag tat gaa aac act aag aca tgt cga ggg cca gat gga    528
Ser Ser Glu Lys Tyr Glu Asn Thr Lys Thr Cys Arg Gly Pro Asp Gly
                165                 170                 175 gaa ctc cat gcc aac ctg ctt tgc cct gtg gat gtg ctg gat gtt ccc    576
Glu Leu His Ala Asn Leu Leu Cys Pro Val Asp Val Leu Asp Val Pro
            180                 185                 190 gag ggc acc ttg cct gac aaa cag agc act gag caa gcc ata cag ttg    624
Glu Gly Thr Leu Pro Asp Lys Gln Ser Thr Glu Gln Ala Ile Gln Leu
        195                 200                 205 ttg gaa aag atg aaa acg tca gcc agt cct ttc ttc ctg gcc gtt ggg    672
Leu Glu Lys Met Lys Thr Ser Ala Ser Pro Phe Phe Leu Ala Val Gly
    210                 215                 220 tat cat aag cca cac atc ccc ttc aga tac ccc aag gaa ttt cag aag    720
Tyr His Lys Pro His Ile Pro Phe Arg Tyr Pro Lys Glu Phe Gln Lys
225                 230                 235                 240 ttg tat ccc ttg gag aac atc acc ctg gcc ccc gat ccc gag gtc cct    768
Leu Tyr Pro Leu Glu Asn Ile Thr Leu Ala Pro Asp Pro Glu Val Pro
                245                 250                 255 gat ggc cta ccc cct gtg gcc tac aac ccc tgg atg gac atc agg caa    816
Asp Gly Leu Pro Pro Val Ala Tyr Asn Pro Trp Met Asp Ile Arg Gln
            260                 265                 270 cgg gaa gac gtc caa gcc tta aac atc agt gtg ccg tat ggt cca att    864
Arg Glu Asp Val Gln Ala Leu Asn Ile Ser Val Pro Tyr Gly Pro Ile
        275                 280                 285 cct gtg gac ttt cag cgg aaa atc cgc cag agc tac ttt gcc tct gtg    912
Pro Val Asp Phe Gln Arg Lys Ile Arg Gln Ser Tyr Phe Ala Ser Val
    290                 295                 300 tca tat ttg gat aca cag gtc ggc cgc ctc ttg agt gct ttg gac gat    960
Ser Tyr Leu Asp Thr Gln Val Gly Arg Leu Leu Ser Ala Leu Asp Asp
305                 310                 315                 320 ctt cag ctg gcc aac agc acc atc att gca ttt acc tcg gat cat ggg   1008
Leu Gln Leu Ala Asn Ser Thr Ile Ile Ala Phe Thr Ser Asp His Gly
                325                 330                 335 tgg gct cta ggt gaa cat gga gaa tgg gcc aaa tac agc aat ttt gat   1056
Trp Ala Leu Gly Glu His Gly Glu Trp Ala Lys Tyr Ser Asn Phe Asp
            340                 345                 350 gtt gct acc cat gtt ccc ctg ata ttc tat gtt cct gga agg acg gct   1104
Val Ala Thr His Val Pro Leu Ile Phe Tyr Val Pro Gly Arg Thr Ala
        355                 360                 365 tca ctt ccg gag gca ggc gag aag ctt ttc cct tac ctc gac cct ttt   1152
Ser Leu Pro Glu Ala Gly Glu Lys Leu Phe Pro Tyr Leu Asp Pro Phe
    370                 375                 380
```

```
gat tcc gcc tca cag ttg atg gag cca ggc agg caa tcc atg gac ctt   1200
Asp Ser Ala Ser Gln Leu Met Glu Pro Gly Arg Gln Ser Met Asp Leu
385                 390                 395                 400 gtg gaa ctt gtg tct ctt ttt ccc acg ctg gct gga ctt gca gga ctg   1248
Val Glu Leu Val Ser Leu Phe Pro Thr Leu Ala Gly Leu Ala Gly Leu
            405                 410                 415 cag gtt cca cct cgc tgc ccc gtt cct tca ttt cac gtt gag ctg tgc   1296
Gln Val Pro Pro Arg Cys Pro Val Pro Ser Phe His Val Glu Leu Cys
        420                 425                 430 aga gaa ggc aag aac ctt ctg aag cat ttt cga ttc cgt gac ttg gaa   1344
Arg Glu Gly Lys Asn Leu Leu Lys His Phe Arg Phe Arg Asp Leu Glu
    435                 440                 445 gag gat ccg tac ctc cct ggt aat ccc cgt gaa ctg att gcc tat agc   1392
Glu Asp Pro Tyr Leu Pro Gly Asn Pro Arg Glu Leu Ile Ala Tyr Ser
450                 455                 460 cag tat ccc cgg cct tca gac atc cct cag tgg aat tct gac aag ccg   1440
Gln Tyr Pro Arg Pro Ser Asp Ile Pro Gln Trp Asn Ser Asp Lys Pro
465                 470                 475                 480 agt tta aaa gat ata aag atc atg ggc tat tcc ata cgc acc ata gac   1488
Ser Leu Lys Asp Ile Lys Ile Met Gly Tyr Ser Ile Arg Thr Ile Asp
            485                 490                 495 tat agg tat act gtg tgg gtt ggc ttc aat cct gat gaa ttt cta gct   1536
Tyr Arg Tyr Thr Val Trp Val Gly Phe Asn Pro Asp Glu Phe Leu Ala
        500                 505                 510 aac ttt tct gac atc cat gca ggg gaa ctg tat ttt gtg gat tct gac   1584
Asn Phe Ser Asp Ile His Ala Gly Glu Leu Tyr Phe Val Asp Ser Asp
    515                 520                 525 cca ttg cag gat cac aat atg tat aat gat tcc caa ggt gga gat ctt   1632
Pro Leu Gln Asp His Asn Met Tyr Asn Asp Ser Gln Gly Gly Asp Leu
530                 535                 540 ttc cag ttg ttg atg cct tga                                       1653
Phe Gln Leu Leu Met Pro
545                 550

<210> SEQ ID NO 10
<211> LENGTH: 550
<212> TYPE: PRT
<213> ORGANISM: Homo sapiens

<400> SEQUENCE: 10

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140
```

```
His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550
```

<210> SEQ ID NO 11
<211> LENGTH: 31
<212> TYPE: DNA
<213> ORGANISM: Artificial Sequence
<220> FEATURE:
<223> OTHER INFORMATION: Primer hMPR9-f, synthetic sequence

<400> SEQUENCE: 11
ataatccatg gttgtcagag tggaagggga c                              31

<210> SEQ ID NO 12
<211> LENGTH: 32
<212> TYPE: DNA
<213> ORGANISM: Artificial Sequence
<220> FEATURE:
<223> OTHER INFORMATION: Primer hMPR9-r, synthetic sequence

<400> SEQUENCE: 12
gcaatgcggc cgcgaaaggt gggcaggcat ac                             32

<210> SEQ ID NO 13
<211> LENGTH: 534
<212> TYPE: DNA
<213> ORGANISM: Artificial Sequence
<220> FEATURE:
<223> OTHER INFORMATION: Synthetic DNA sequence encoding hMPR9 having
      Bip signal at its N-terminus and His-tag at the C-terminus

<400> SEQUENCE: 13
atgaagttat gcatattact ggccgtcgtc gcctttgttg gcctctcgct cgggagcgct      60
gttgtcagag tggaagggga caactgtgag gtgaaagacc caaggcatgg caacttgtat     120
gacctgaagc ccctgggcct caacgacacc atcgtgagcg ctggcgaata cacttattac     180
ttccgggtct gtgggaagct ttcctcagac gtctgcccca caagtgacaa gtccaaggtg     240
gtctcctcat gtcaggaaaa gcgggaaccg cagggatttc acaaagtggc aggtctcctg     300
actcagaagc taacttatga aaatggcttg ttaaaaatga acttcacggg ggggacact      360 tgccataagg tttatcagcg ctccacagcc atcttcttct actgtgaccg cggcacccag     420
cggccagtat ttctaaagga gacttcagat tgttcctact tgtttgagtg gcgaacgcag     480
tatgcctgcc caccttttcgg atccggcgcg ccacatcacc atcaccatca ctga         534

<210> SEQ ID NO 14
<211> LENGTH: 45
<212> TYPE: DNA
<213> ORGANISM: Artificial Sequence
<220> FEATURE:
<223> OTHER INFORMATION: Primer hMPR9-f2, synthetic sequence

<400> SEQUENCE: 14
gttggcctct cgctcgggag cgctgttgtc agagtggaag ggac                45

<210> SEQ ID NO 15
<211> LENGTH: 68
<212> TYPE: DNA
<213> ORGANISM: Artificial Sequence
<220> FEATURE:
<223> OTHER INFORMATION: Primer hMPR9-r2, synthetic sequence

<400> SEQUENCE: 15
ataatgcggc cgctcagtga tggtgatggt gatgtggcgc gccggatccg aaaggtgggc      60
aggcatac                                                              68

```
<210> SEQ ID NO 16
<211> LENGTH: 73
<212> TYPE: DNA
<213> ORGANISM: Artificial Sequence
<220> FEATURE:
<223> OTHER INFORMATION: Primer hMPR9-f3, synthetic sequence

<400> SEQUENCE: 16
ataatccatg ggatatctaa taaatatgaa gttatgcata ttactggccg tcgtcgcctt        60
tgttggcctc tcg                                                          73

<210> SEQ ID NO 17
<211> LENGTH: 68
<212> TYPE: DNA
<213> ORGANISM: Artificial Sequence
<220> FEATURE:
<223> OTHER INFORMATION: Primer hMPR9-r3, synthetic sequence

<400> SEQUENCE: 17
ataatgcggc cgctcagtga tggtgatggt gatgtggcgc gccggatccg aaaggtgggc        60
aggcatac                                                                68
```

METHOD FOR PRODUCTION OF RECOMBINANT HUMAN IDURONATE 2-SULFATASE

The instant application is a national stage application of PCT/JP2012/000365, filed Jan. 23, 2012.

TECHNICAL FIELD

The present invention relates to a method for production of recombinant human iduronate 2-sulfatase (rhI2S) (the 26th to 550th amino acids of SEQ ID NO: 10). More specifically the present invention relates to a process for production of rhI2S (the 26th to 550th amino acids of SEQ ID NO: 10) by culturing rhI2S (the 26th to 550th amino acids of SEQ ID NO: 10) producing mammalian cells in a serum free medium, as well as to a process for purification of rhI2S (the 26th to 550th amino acids of SEQ ID NO: 10) obtained in the culture supernatant through column chromatography, in high yield and to such a high purity as permits direct use of the purified protein as a medical drug. The present invention further relates to glycosylated rhI2S (the 26th to 550th amino acids of SEQ ID NO: 10) which is characterized as having an ability to undergo highly efficient cellular uptake, strong affinity for the mannose-6-phosphate (M6P) receptor, and as having a linked oligosaccharide chain with high mannose-6-phosphate content.

BACKGROUND ART

Iduronate 2-sulfatase (I2S) is a lysosomal enzyme having an activity to hydrolyze a sulfate ester bond in a glycosaminoglycan molecule such as heparan sulfate and dermatan sulfate. Patients of Hunter's syndrome genetically lack I2S activity. Lack of this enzyme causes abnormal metabolism of heparan sulfate and dermatan sulfate, which then leads to accumulation of fragments of the latter molecules in tissues such as the liver and kidney, and also to excretion of heparan sulfate and dermatan sulfate in urine. These abnormalities then cause diverse symptoms in patients suffering Hunter's syndrome, including skeletal deformities and severe mental retardation.

The fact that the patients suffering Hunter's syndrome show scarce I2S activity has already been known since 1970's, and an abnormality of I2S gene was expected to be the cause of this disease. In 1999, human gene encoding I2S was isolated and confirmed to be the responsible gene for this disease (see LPL 1).

Based on the fact mentioned above, I2S replacement has been attempted since 1970's to improve the clinical conditions of the patients, including transplantation of normal macrophage (see LPL 2) and infusion of normal serum (see LPL 3) to supplement I2S activity in the patients. The results of those attempts showed that the concentration of heparan sulfate in patients' urine decreased by the supplementation of I2S activity, suggesting that I2S replacement therapy should have a clinical efficacy against Hunter's syndrome, though improvement in clinical symptoms was not confirmed. Practical application of the I2S replacement therapy, however, has been extremely limited due to the lack of supply of this enzyme.

Isolation of the gene encoding I2S in 1999 made it possible to produce I2S in a large scale using recombinant technology, and to use this enzyme as a medicament for the enzyme replacement therapy for Hunter's syndrome (see PTL 1). However a method has not been reported so far for providing I2S with such a high purity as is sufficient for the enzyme to be directly used as a medical drug.

CITATION LIST

Patent Literature

[PTL 1]
U.S. Pat. No. 5,932,211

Non Patent Literature

[NPL 1]
Wilson P J et al., Proc Natl Acad Sci USA. 87: 8531-5, 1990.
[NPL 2]
Dean M F et al., J Clin Invest. 63: 138-45, 1979.
[NPL 3]
Brown F R 3$^{rd}$ et al., Am J Med Genet. 13 309-18, 1982.

SUMMARY OF INVENTION

Technical Problem

Against the above background, it is an objective of the present invention to provide a method for production of recombinant human I2S (rhI2S) (the 26th to 550th amino acids of SEQ ID NO: 10) starting with culturing of rhI2S (the 26th to 550th amino acids of SEQ ID NO: 10) producing mammalian cells in a serum free medium.

It is another objective of the present invention to provide a process for purification of rhI2S (the 26th to 550th amino acids of SEQ ID NO: 10) obtained in the culture supernatant, through column chromatography, in high yield and to such a high purity as permits direct use of the purified protein as a medical drug.

Solution to Problem

The present inventors found that rhI2S (the 26th to 550th amino acids of SEQ ID NO: 10) contained in the supernatant of a culture of rhI2S (the 26th to 550th amino acids of SEQ ID NO: 10)-producing cells in a serum-free medium, can be purified to a very high purity, and in a very high yield as well, by subjecting the rhI2S (the 26th to 550th amino acids of SEQ ID NO: 10) to a purification process consisting of a combination of cation-exchange column chromatography, dye-affinity column chromatography, anion-exchange column chromatography, chromatography using a column having affinity for phosphate group, and gel filtration column chromatography. The present invention was completed through further studies based on the finding.

Thus, the present invention provides what follows:
1. A method for production of recombinant human iduronate 2-sulfatase (rhI2S) (the 26th to 550th amino acids of SEQ ID NO: 10) comprising the steps of:
    (a) culturing rhI2S (the 26th to 550th amino acids of SEQ ID NO: 10)-producing mammalian cells in a serum-free medium to let them secrete rhI2S (the 26th to 550th amino acids of SEQ ID NO: 10) in the medium,
    (b) collecting culture supernatant by removing the cells from the culture that is obtained in step (a) above,
    (c) subjecting the culture supernatant collected in step (b) above to cation-exchange column chromatography to collect rhI2S (the 26th to 550th amino acids of SEQ ID NO: 10)-active fractions, (d) subjecting the fractions collected in step (c) above to dye affinity column chromatography to collect rhI2S (the 26th to 550th amino acids of SEQ ID NO: 10)-active fractions, (e) subjecting the fractions collected in step (d) above to anion-exchange column chromatography to collect rhI2S (the 26th to 550th amino acids of SEQ ID NO: 10)-active fractions, (f) subjecting the fractions collected in step (e) above to a column chromatography employing as solid phase a material having affinity for phosphate group to collect rhI2S (the 26th to 550th amino acids of SEQ ID NO: 10)-active fractions, and (g) subjecting the fractions collected in step (0 above to gel filtration column chromatography to collect rhI2S (the 26th to 550th amino acids of SEQ ID NO: 10)-active fractions, in the order.

2. The method according to (1) above, wherein the cation exchanger employed in the cation-exchange column chromatography is a weak cation exchanger.

3. The method according to (2) above, wherein the weak cation exchanger has a selectivity based on both hydrophobic interaction and hydrogen bond formation.

4. The method according to (2) or (3) above, wherein the weak cation exchanger has phenyl groups, amide bonds and carboxyl groups.

5. The method according to one of (1) to (4) above, wherein the dye employed in the dye affinity column chromatography is a blue triazine dye.

6. The method according to one of (1) to (5) above, wherein the material having affinity for phosphate group is selected from the group consisting of fluoroapatite and hydroxyapatite.

7. The method according to (6) above, wherein the material having affinity to phosphate group is fluoroapatite.

8. The method according to one of (1) to (7) above, wherein the mammalian cells are CHO cells transfected with an expression vector which is designed to express rhI2S (the 26th to 550th amino acids of SEQ ID NO 10) under the regulation of EF-1(alpha) promoter.

9. A method for purification of rhI2S (the 26th to 550th amino acids of SEQ ID NO: 10) from contaminants, wherein the rhI2S (the 26th to 550th amino acids of SEQ ID NO: 10) has an oligosaccharide chain linked thereto containing one or more mannose 6-phosphate residues, and wherein the method comprises the steps of (a) applying rhI2S (the 26th to 550th amino acids of SEQ ID NO 10) with contaminants to a chromatography column which employs as solid phase a material having affinity for phosphate group, (b) flowing a first mobile phase through the column to wash the column while letting rhI2S (the 26th to 550th amino acids of SEQ ID NO: 10) be adsorbed by the column, and (c) eluting rhI2S (the 26th to 550th amino acids of SEQ ID NO: 10) from the column by flowing a second mobile phase through the column, wherein the second mobile phase contains a phosphate at higher concentration than the first mobile phase.

10. The method according to (9) above, wherein the material having affinity for phosphate group is selected from the group consisting of fluoroapatite and hydroxyapatite.

11. The method according to (10) above, wherein the material having affinity for phosphate group is fluoroapatite.

12. RhI2S (the 26th to 550th amino acids of SEQ ID NO: 10) having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 3.5 to 6.0.

13. RhI2S (the 26th to 550th amino acids of SEQ ID NO: 10) according to (12) above having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 3.6 to 5.5.

14. RhI2S (the 26th to 550th amino acids of SEQ ID NO: 10) according to (12) above having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 3.7 to 5.4.

15. RhI2S (the 26th to 550th amino acids of SEQ ID NO: 10) according to (12) above having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 4.0 and 6.0.

16. RhI2S (the 26th to 550th amino acids of SEQ ID NO: 10) according to (12) above having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 4.2 and 5.8.

17. RhI2S (the 26th to 550th amino acids of SEQ ID NO: 10) according to (12) above having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is in the range of 4.5 and 5.4.

18. RhI2S (the 26th to 550th amino acids of SEQ ID NO: 10) according to one of (12) to (17) above, wherein the average dissociation constant between the rhI2S (the 26th to 550th amino acids of SEQ ID NO: 10) and mannose-6-phosphate receptor is in the range of 7.5 to $20 \times 10^{-10}$ mol/L.

19. RhI2S (the 26th to 550th amino acids of SEQ ID NO: 10) according to one of (12) to (17) above, wherein the average dissociation constant between the rhI2S (the 26th to 550th amino acids of SEQ ID NO: 10) and mannose-6-phosphate receptor is in the range of 7.5 to $15 \times 10^{-10}$ mol/L.

20. RhI2S (the 26th to 550th amino acids of SEQ ID NO: 10) according to one of (12) to (17) above, wherein the average dissociation constant between the rhI2S (the 26th to 550th amino acids of SEQ ID NO: 10) and mannose-6-phosphate receptor is in the range of 4.5 to $20 \times 10^{-10}$ mol/L.

21. RhI2S (the 26th to 550th amino acids of SEQ ID NO: 10) according to one of (12) to (17) above, wherein the average dissociation constant between the rhI2S (the 26th to 550th amino acids of SEQ ID NO: 10) and mannose-6-phosphate receptor is in the range of 5.0 to $15 \times 10^{-10}$ mol/L.

22. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 3.5 to 6.0.

23. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 3.6 to 5.5.

24. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 3.7 to 5.4.

25. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 4.0 to 6.0.

26. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 4.2 to 5.8.

27. RhI2S (the 26th to 550th amino acids of SEQ ID NO: 10) produced by the method according to one of (1) to (11) above, wherein the rhI2S (the 26th to 550th amino acids of SEQ ID NO: 10) has an oligosaccharide chain linked thereto containing one or more mannose-6-phosphate residues, and wherein the average number of the mannose-6-phosphate residues per rhI2S (the 26th to 550th amino acids of SEQ ID NO: 10) molecule is in the range of 4.5 to 5.4.

28. RhI2S (the 26th to 550th amino acids of SEQ ID NO: 10) produced by the method according to one of (1) to (11) above, wherein the average dissociation constant between the rhI2S (the 26th to 550th amino acids of SEQ ID NO: 10) and mannose-6-phosphate receptor is in the range of 7.5 to $20 \times 10^{-10}$ mol/L.

29. RhI2S (the 26th to 550th amino acids of SEQ ID NO: 10) produced by the method according to one of (1) to (11) above, wherein the average dissociation constant between the rhI2S (the 26th to 550th amino acids of SEQ ID NO: 10) and mannose-6-phosphate receptor is in the range of 7.5 to $15 \times 10^{-10}$ mol/L.

30. RhI2S (the 26th to 550th amino acids of SEQ ID NO: 10) produced by the method according to one of (1) to (11) above, wherein the average dissociation constant between the rhI2S (the 26th to 550th amino acids of SEQ ID NO: 10) and mannose-6-phosphate receptor is in the range of 4.5 to $20 \times 10^{-10}$ mol/L.

31. RhI2S (the 26th to 550th amino acids of SEQ ID NO: 10) produced by the method according to one of (1) to (11), wherein the average dissociation constant between the rhI2S (the 26th to 550th amino acids of SEQ ID NO: 10) and mannose-6-phosphate receptor is in the range of 5.0 to $15 \times 10^{-10}$ mol/L.

32. RhI2S (the 26th to 550th amino acids of SEQ ID NO: 10) produced by the method according to one of (1) to (11) above.

Advantageous Effects of Invention

As it has enabled to produce rhI2S (the 26th to 550th amino acids of SEQ ID NO: 10) starting with serum-free culturing of cells, the present invention provides rhI2S (the 26th to 550th amino acids of SEQ ID NO: 10) which is free of any serum-derived contaminants including pathogenic agents such as viruses or prions. Therefore, the rhI2S (the 26th to 550th amino acids of SEQ ID NO: 10) obtained according to the present invention can be administered into a human body as a safe medicament substantially without any risks of exposure to such pathogenic agents. Further, as it has enabled purification of rhI2S (the 26th to 550th amino acids of SEQ ID NO: 10) substantially avoiding any use of organic solvents, the present invention eliminates the risk of denaturation of rhI2S (the 26th to 550th amino acids of SEQ ID NO: 10) which otherwise might be caused by the exposure to an organic solvent employed. Furthermore, the present invention is favorable to the environment, for the waste fluid left after performing the purification process according to it does not contain an organic solvent, and in the economic sense as well, for it requires no facility in which to treat organic solvents which would otherwise be contained in the waste fluid.

Further the present invention makes it possible to selectively purify rhI2S (the 26th to 550th amino acids of SEQ ID NO: 10) having mannose 6-phosphate residue in its oligosaccharide chain. To exert its enzymatic activity after administration to a human body, rhI2S (the 26th to 550th amino acids of SEQ ID NO: 10) should be taken up by relevant cells through mannose 6-phosphate receptors expressed on their surface. Therefore the efficacy of rhI2S (the 26th to 550th amino acids of SEQ ID NO: 10) as a medicament is dramatically increased through the selective purification of rhI2S (the 26th to 550th amino acids of SEQ ID NO: 10) according to the present invention.

BRIEF DESCRIPTION OF DRAWINGS

FIG. 1-2 shows a second part of a schematic diagram illustrating the method for construction of vector pE-neo/hGHpA(I2S).

FIG. 2 shows the growth curve of recombinant cells for expression of rhI2S (the 26th to 550th amino acids of SEQ ID NO: 10).

DESCRIPTION OF EMBODIMENTS

Figure 1:
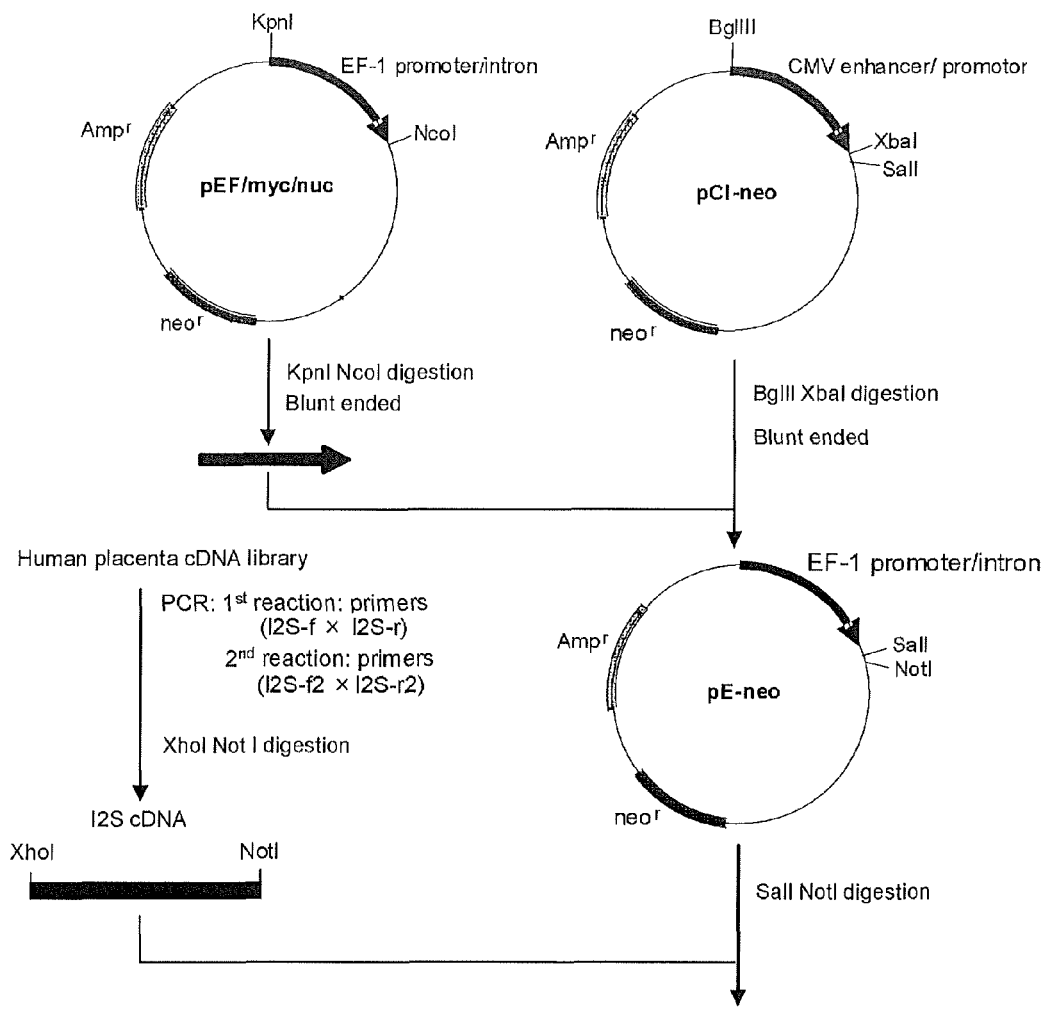
FIG. 1-1 shows a first part of a schematic diagram illustrating the method for construction of vector pE-neo/hGHpA (I2S).

In the present invention, while recombinant human iduronate 2-sulfatase (rhI2S) (the 26th to 550th amino acids of SEQ ID NO: 10) is preferably a recombinant protein of human wild-type I2S comprising a single glycosylated polypeptide composed of 525 amino acids, it does not exclude recombinant proteins of human mutant-type I2S's, which have one or more substitution, deletion, addition, and insertion of one or more amino acids compared with the amino acid sequence of human wild-type I2S. The amino acid sequence of human wild-type I2S, including an N-terminal signal sequence, and the DNA sequence encoding it are shown as SEQ ID NO:9 and SEQ ID NO:10, respectively. The N-terminal signal sequence consists of 25 amino acids and is removed post-translationally.

In the present invention, the term "recombinant human I2S-producing mammalian cells" or "rhI2S (the 26th to 550th amino acids of SEQ ID NO: 10)-producing mammalian cells" means mammalian cells which have been artificially manipulated to express, or strongly express, the gene encoding human I2S. Though in general the gene to be strongly expressed is one which is introduced to the mammalian cells (transformation) using an expression vector in which the gene is incorporated, it may be also an intrinsic gene which has been artificially modified in such a manner that the gene comes to be strongly expressed. Examples of the means for artificially modifying an intrinsic gene to make it strongly express itself include, but not limited to, replacement of the promoter upstream of the intrinsic gene with a promoter which strongly induces expression of the gene. Such methods have been disclosed in several literatures (e.g., WO94/12650, and WO95/31560). Though there is no particular limitation as to which mammalian cells are to be employed, preferred are those of human-, mouse- or hamster-origin, and, among others, CHO cells, which originate from Chinese hamster ovary cells, are particularly preferred.

In the present invention, the term "recombinant human I2S" or "rhI2S (the 26th to 550th amino acids of SEQ ID NO: 10)" means the human I2S which is secreted by the above-mentioned rhI2S (the 26th to 550th amino acids of SEQ ID NO: 10)-producing mammalian cells in the medium during culture.

In the present invention, the term "oligosaccharide chain" means a chain of oligosaccharide covalently linked to the peptide chain of I2S, including an asparagine type sugar chain, which is covalently bound to an asparagine residue of I2S.

As used in the present invention, the term "fluoroapatite" means a material comprising an insoluble fluoridated mineral of calcium phosphate with the chemical formula $Ca_5(PO_4)_3F$. Apart from the compound which naturally occurs, fluoroapatite is artificially produced by replacing the hydroxyl groups of hydroxylapatite ($Ca_5(PO_4)_3OH$), and products in which the hydroxyl groups are almost completely replaced with fluoride ions are commercially available (e.g., CFT Type II 40 micrometer (Bio-Rad Laboratories).

In the present invention, an example of preferable serum-free media in which the rhI2S (the 26th to 550th amino acids of SEQ ID NO: 10)-producing mammalian cells are to be cultured is the following medium which comprises; 3-700 mg/mL of amino acids, 0.001-50 mg/L of vitamins, 0.3-10 g/L of monosaccharides, 0.1-10000 mg/L of inorganic salts, 0.001-0.1 mg/L of trace elements, 0.1-50 mg/L of nucleosides, 0.001-10 mg/L of fatty acids, 0.01-1 mg/L of biotin, 0.1-20 micrograms/L of hydrocortisone, 0.1-20 mg/L of insulin, 0.1-10 mg/L of vitamin $B_{12}$, 0.01-1 mg/L of putrescine, 10-500 mg/L of sodium pyruvate, and water-soluble iron compounds. As desired, it may also include thymidine, hypoxanthine, a conventional pH indicator, and antibiotics.

Further, DMEM/F12 medium, a mixed medium consisting of DMEM and F12, may also be used as a basic serum-free medium. Both of these media are well known to those skilled in the art. As a serum-free medium, DMEM(HG)HAM modified (R5) medium may be used, too, which contains sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium.

Each of the chromatography procedures for purification of the rhI2S (the 26th to 550th amino acids of SEQ ID NO: 10) may, when needed, be carried out in the presence of a non-ionic surfactant in order to prevent nonspecific binding of the protein. Though there is no particular limitation as to which nonionic surfactant is to be employed, a polysorbate-based surfactant is preferably employed, and more preferably polysorbate 80 or polysorbate 20. The concentration of such a nonionic surfactant is preferably 0.005% (w/v) to 0.05% (w/v), more preferably 0.01% (w/v).

The process for purification of the rhI2S (the 26th to 550th amino acids of SEQ ID NO: 10) may be carried out at room temperature or at lower temperatures, but preferably at lower temperatures, particularly at 1-10 deg C.

In the first chromatography step for the purification process, the rhI2S (the 26th to 550th amino acids of SEQ ID NO: 10) is let bind to the cationic-exchange column that has been equilibrated with an acetate buffer supplemented with a salt. The pH of this acetate buffer has been adjusted preferably to 4.0-4.6, more preferably to about 4.2-4.4, and still more preferably to about 4.3. Though there is no particular limitation as to which salt is to be added to the phosphate buffer, sodium chloride is preferred, and its concentration is preferably in the range of 50-250 mM, and more preferably in the range of 100-200 mM.

After the column to which rhI2S (the 26th to 550th amino acids of SEQ ID NO: 10) is bound is washed, the rhI2S (the 26th to 550th amino acids of SEQ ID NO: 10) is eluted using an acetate buffer with an increased pH, preferably in the range of about 4.8-6.5, more preferably in the range of about 5.0-5.4 and still more preferably about 5.1. Salt should be contained in this acetate buffer. Though there is no particular limitation as to which salt should be contained to the acetate buffer, sodium chloride is preferred, and its concentration is preferably in the range of 50-250 mM, and more preferably in the range of 100-200 mM.

Further, though there is no particular limitation as to which cation-exchanger is to be employed in the cation-exchange column chromatography, a weak cation exchanger is preferred, and more preferred is a weak cation exchanger having a selectivity based on both hydrophobic interaction and hydrogen bond formation. For example, a weak cation exchanger having phenyl groups, amide bonds and carboxyl groups and having a selectivity based on both hydrophobic interaction and hydrogen bond formation, such as Capto MMC (GE Healthcare), etc., may be employed.

The dye affinity chromatography, the second step of the purification process, is a step for removing contaminants making use of the strong affinity of human I2S to certain dyes. Blue triazine dye is preferably used, but other triazine dyes are also suitable. A particularly preferred column material for this is Blue Sepharose 6 FF, Fast Flow (GE Healthcare) in which the dye, Cibacron™ Blue F3GA, is covalently immobilized to Sepharose 6 Fast Flow matrix.

The dye affinity chromatography column is equilibrated with an acetate buffer supplemented with a salt. The pH of this acetate buffer has been adjusted preferably to 4.5-5.5, more preferably to about 4.8-5.2, and still more preferably to about 5.0. Though there is no particular limitation as to which salt is to be added to the phosphate buffer, sodium chloride is preferred, and its concentration is preferably in the range of 50-200 mM, and more preferably in the range of 80-120 mM.

RhI2S (the 26th to 550th amino acids of SEQ ID NO: 10)-containing fractions of the eluate obtained in the first step are diluted with 1-2 volumes of water, and adjusted preferably at pH 4.5-5.5, more preferably at pH 4.8-5.2, and still more preferably at about pH 5.0, then the eluate are applied to the column.

After the column to which rhI2S (the 26th to 550th amino acids of SEQ ID NO: 10) is bound is washed, the rhI2S (the 26th to 550th amino acids of SEQ ID NO: 10) is eluted. Elution may be done by an acetate buffer with an increased pH. The concentration of a salt in the buffer may be increased at the same time. The pH of this acetate buffer has been adjusted preferably to 5.5-6.5, more preferably to 5.8-6.2, and further preferably to about 6.0. In the case the concentration of a salt is also increased, its concentration is preferably in the range of 100-200 mM, more preferably in the range of 120-170 mM, and still more preferably about 150 mM.

The anion-exchange column chromatography, the third step of the purification process, is a step to eliminate contaminant proteins. Though there is no particular limitation as to which anion-exchanger resin is to be employed, strong anion-exchanger resin may be used preferably. Commercially available resins, such as Q Sepharose Fast Flow (GE Healthcare), may be used preferably.

In the anion-exchange column chromatography, the column is equilibrated with a phosphate buffer supplemented with a salt. The pH of this phosphate buffer has been adjusted preferably to 5.0-6.0, more preferably to about 5.2-5.8, and still more preferably to about 5.5. Though there is no particular limitation as to which salt is to be added to the phosphate buffer, sodium chloride is preferred, and its concentration is preferably in the range of 100-200 mM, more preferably in the range of 120-180 mM, and still more preferably about 150 mM.

pH of the rhI2S (the 26th to 550th amino acids of SEQ ID NO: 10)-containing fractions of the eluate obtained in the second step is adjusted preferably to 5.0-6.0, more preferably to pH 5.2-5.8, and further preferably to about pH 5.5. The eluate then is applied to the column.

After the anion-exchanger column to which rhI2S (the 26th to 550th amino acids of SEQ ID NO: 10) is bound is washed, the rhI2S (the 26th to 550th amino acids of SEQ ID NO: 10) is eluted using a phosphate buffer with increased salt concentration, preferably to 300-500 mM, more preferably to 350-450 mM, and still more preferably to about 400 mM.

The column chromatography employing a solid phase having affinity to phosphate group, the fourth step of the purification, is a step to eliminate not only contaminant proteins but also such rhI2S (the 26th to 550th amino acids of SEQ ID NO: 10) molecules that have a oligosaccharide chain containing comparatively few mannose 6-phosphate residues. Though there is no particular limitation as to which solid phase is to be used having affinity for phosphate group, fluoroapatite and hydroxyapatite may preferably be used, and fluoroapatite is particularly preferred.

Fluoroapatite has affinity for a phosphate group on the oligosaccharide chain. Thus, the more mannose 6-phosphate residues rhI2S (the 26th to 550th amino acids of SEQ ID NO: 10) has in its oligosaccharide chain, the more selectively it is bound to fluoroapatite. Though there is no particular limitation as to which fluoroapatite is to be employed as the solid phase, commercially available fluoroapatite, such as CFT Type II 40 micrometer (Bio-Rad Laboratories), may be used preferably.

The fluoroapatite column is equilibrated with a phosphate buffer supplemented with a salt. The pH of this phosphate buffer has been adjusted preferably to 6.0-7.0, more preferably to about 6.3-6.7, and still more preferably to about 6.5, and the concentration of phosphate preferably to 4.0-15.0 mM, more preferably to about 5.0-10.0 mM, and further preferably to about 7.5 mM. Though there is no particular limitation as to which salt is to be added to the phosphate buffer, sodium chloride is preferred, and its concentration is preferably in the range of 300-500 mM, and more preferably in the range of 350-450 mM.

RhI2S (the 26th to 550th amino acids of SEQ ID NO: 10)-containing fractions of the eluate obtained in the third step are diluted with 2-4 volumes of water, and adjusted preferably to pH 6.0-7.0, more preferably to pH 6.3-6.7, and still more preferably to about pH 6.5, and this diluted eluate then are applied to the column.

After the column to which rhI2S (the 26th to 550th amino acids of SEQ ID NO: 10) is bound is washed, the rhI2S (the 26th to 550th amino acids of SEQ ID NO: 10) is eluted. Elution may be done by a phosphate buffer containing a salt. The pH of this phosphate buffer has been adjusted preferably to 6.0-7.0, more preferably to about 6.3-6.7, and still more preferably to about 6.5, and the concentration of phosphate is adjusted preferably to 100 to 200 mM, more preferably to about 125-175 mM, and still more preferably to about 150 mM. Though there is no particular limitation as to which salt is to be used, potassium chloride may preferably be used, at a concentration preferably of 50-250 mM, more preferably of 100-200 mM, and still more preferably of about 150 mM.

The gel filtration column chromatography, the fifth step of the purification process, is a step for elimination of low molecular-weight impurities, such as endotoxins, as well as multimeric complexes or decomposition products of rhI2S (the 26th to 550th amino acids of SEQ ID NO: 10). Thus, substantially pure rhI2S (the 26th to 550th amino acids of SEQ ID NO: 10) is obtained through these consecutive steps, from the first to the fifth.

A step for virus inactivation may optionally be added to the purification process of the present invention. Though there is no particular limitation as to which process for virus inactivation is to be applied, solvent-detergent method may preferably be applied. For this, nonionic surfactant is added to a solution containing rhI2S (the 26th to 550th amino acids of SEQ ID NO: 10), and the mixture is incubated for more than 3 hours. Though there is no particular limitation as to which surfactant is to be used, polysorbate 20, polysorbate 80, tritonX-100, and tri(n-butyl)phosphate may preferably be used alone or in any combination, and more preferably the combination of polysorbate 80 and tri(n-butyl)phosphate may be used.

Such an additional step for virus inactivation may be interposed between any two adjacent steps of the purification process mentioned above, particularly between the second and third steps of the purification process (i.e., the step of dye affinity chromatography and that of anion-exchange column chromatography).

In the present invention, the method for production of rhI2S (the 26th to 550th amino acids of SEQ ID NO: 10) includes at least a step in which fractions containing rhI2S (the 26th to 550th amino acids of SEQ ID NO: 10) is subjected to column chromatography using a solid phase having affinity for phosphate group, where, as such a solid phase, fluoroapatite and hydroxyapatite may preferably be used, of which fluoroapatite is particularly preferred. The step, using a solid phase having affinity for phosphate group, is employed for preferentially purifying rhI2S (the 26th to 550th amino acids of SEQ ID NO: 10) containing a greater number of mannose 6-phosphate residues in its oligosaccharide chain. The step can be employed in combination with at least one other purification step chosen from cation-exchange column chromatography, dye-affinity column chromatography, anion-exchange column chromatography, and gel filtration column chromatography, in any order. A combination is preferred which consists of cation-exchange column chromatography, dye-affinity column chromatography, anion-exchange column chromatography, and then column chromatography using a solid phase having affinity for phosphate group, in this order. More preferred is a combination consisting of cation-exchange column chromatography, dye-affinity column chromatography, anion-exchange column chromatography, column chromatography employing a solid phase having affinity for phosphate group, and then gel filtration column chromatography, in this order.

The present invention provides rhI2S (the 26th to 550th amino acids of SEQ ID NO: 10) having an oligosaccharide chain linked thereto which contains one or more mannose-6-phosphate residues, wherein the average number of the mannose-6-phosphate residues per rhI2S (the 26th to 550th amino acids of SEQ ID NO: 10) molecule is preferably in the range of 3.5 to 6.5, more preferably 3.5 to 6.0, still more preferably 3.6 to 5.5, further more preferably 3.7 to 5.4. Alternatively, the average number of the mannose-6-phosphate residues per rhI2S (the 26th to 550th amino acids of SEQ ID NO: 10) molecule is preferably in the range of 4.0 to 6.5, more preferably 4.0 to 6.0, still more preferably 4.2 to 5.8, further more preferably 4.5 to 5.4. The number of the mannose-6-phosphate residues per rhI2S (the 26th to 550th amino acids of SEQ ID NO: 10) molecule can be determined by the method described below.

The present invention further provides rhI2S (the 26th to 550th amino acids of SEQ ID NO: 10), wherein the average dissociation constant between the rhI2S (the 26th to 550th amino acids of SEQ ID NO: 10) and mannose-6-phosphate receptor is preferably in the range of 7.0 to $25 \times 10^{-10}$ mol/L, more preferably 7.5 to $20 \times 10^{-10}$ mol/L, still more preferably 7.5 to $15 \times 10^{-10}$ mol/L, and further more preferably 7.5 to $13 \times 10^{-10}$ mol/L. Alternatively, the average dissociation constant between the rhI2S (the 26th to 550th amino acids of SEQ ID NO: 10) and mannose-6-phosphate receptor is preferably in the range of 4.5 to $20 \times 10^{-10}$ mol/L, more preferably 7.5 to $20 \times 10^{-10}$ mol/L, still more preferably 5.0 to $15 \times 10^{-10}$ mol/L, and further more preferably 7.5 to $13 \times 10^{-10}$ mol/L. The dissociation constant can be determined by the method described below.

RhI2S (the 26th to 550th amino acids of SEQ ID NO: 10) described above can be purified by a purification process described in detail below including at least a step in which fractions containing rhI2S (the 26th to 550th amino acids of SEQ ID NO: 10) is subjected to column chromatography using a solid phase having affinity for phosphate groups. Preferable examples of such a solid phase include fluoroapatite and hydroxyapatite, of which fluoroapatite is more preferred.

As an rhI2S (the 26th to 550th amino acids of SEQ ID NO: 10) molecule is incorporated into its target cells through its binding to the M6P receptor expressed on the surface of the cells, rhI2S (the 26th to 550th amino acids of SEQ ID NO: 10) provided by the present invention can be sorted into the target cells more efficiently.

The present invention is described in further detail below with reference to examples. However, it is not intended that the present invention be limited to the examples.

Example 1

1. Construction of Human I2S Expression Vector

Vector pEF/myc/nuc (Invitrogen) was digested with KpnI and NcoI to cut out a region including the EF-1(alpha) promoter and its first intron, which then was blunt-ended with T4 DNA polymerase. Vector pCI-neo (Invitrogen) was digested with BglII and XbaI to cut out a region including the CMV enhancer/promoter and the chimeric intron, which then was blunt-ended with T4 DNA polymerase. Into this was inserted the above-mentioned region including the EF-1(alpha) promoter and its first intron to give pE-neo vector (FIG. 1).

Using a human placenta cDNA library (Takara Bio) as a template, a nested PCR reaction was performed with two sets of primers, composed of a set of outer primers:

```
(a) I2S-f:
                                        (SEQ ID NO: 1)
    5'-ACGCCTATTGCTGCAGGATG-3',
and (b) I2S-r:
                                        (SEQ ID NO: 2)
    5'-AAACGACCAGCTCTAACTCC-3'
``` for the 1st reaction, and a set of two inner primers:

```
(c) I2S-f2:
                                        (SEQ ID NO: 3)
    5'-ATActcgagGCCACCATGCCGCCACCCCGG-3',
and (d) I2S-r2:
                                        (SEQ ID NO: 4)
    5'-TTCTTATgcggccgcTCAAGGCATCAACAA-3'
``` for the 2nd reaction to amplify the DNA fragment containing human I2S cDNA. The PCR fragment thus amplified was digested with XhoI (corresponding to the part shown with lower case letters in SEQ ID NO:3) and NotI (corresponding to the part shown with lower case letters in SEQ ID NO:4) and inserted between SalI and NotI sites of vector pE-neo to give vector pE-neo(I2S) (FIG. 1).

The DNA fragment containing poly adenylation signal sequence of human growth hormone gene was synthesized by annealing four synthetic oligonucleotides:

(a) hGH-f1:
(SEQ ID NO: 5)
5'-GGCCGCTCTAGACCCGGGTGGCATCCCTGTGACCCCTCCCCAGTG

CCTCTCCTGGCCCTGGAAGTTGCCACTCCAGTGCCCACCAGCCTTGTC

CTAATAAA-3', (b) hGH-r1:
(SEQ ID NO: 6)
5'-TGATGCAACTTAATTTTATTAGGACAAGGCTGGTGGGCACTGGAG

TGGCAACTTCCAGGGCCAGGAGAGGCACTGGGGAGGGGTCACAGGGAT

GCCACCCGGGTCTAGAGC-3', (c) hGH-f2:
(SEQ ID NO: 7)
5'-ATTAAGTTGCATCATTTTGTCTGACTAGGTGTCCTTCTATAATAG

CGCAGCACCATGGCCTGAAATAACCTCTGAAAGAGGAACTTGGTTAGG

TAC-3',
and (d) hGH-r2:
(SEQ ID NO: 8)
5'-CTAACCAAGTTCCTCTTTCAGAGGTTATTTCAGGCCATGGTGCTG

CGCTATTATAGAAGGACACCTAGTCAGACAAAA-3'.

The DNA fragment prepared above was inserted between NotI and KpnI sites of pE-neo(I2S) to give pE-neo/hGHpA (I2S), in which I2S cDNA was located downstream of EF-1 promoter and upstream of poly adenylation signal sequence of human growth hormone gene (FIG. 1-1).

Example 2

2. Production of Recombinant Cells for Expression of Human I2S

CHO cells (CHO-K1: purchased from American Type Culture Collection) was transfected with the above-mentioned expression vector pE-neo/hGHpA(I2S) using Lipofectamine2000 (Invitrogen) according to the following method. Briefly, on the day before transfection, $1 \times 10^6$ CHO-K1 cells were seeded in a 3.5-cm culture dish containing 3 mL of D-MEM/F12 medium containing 5% FCS (D-MEM/F12/5% FCS), and the cells were cultured overnight at 37 deg C in a humidified atmosphere of 5% $CO_2$ and 95% air. On the following day, the cells were transfected with 300 microliters of a 1:1 mixture solution consisting of Lipofectamine 2000 solution diluted 25 times with Opti-MEM I medium (Invitrogen) and a plasmid DNA solution pE-neo/hGHpA(I2S) diluted with Opti-MEM I medium to 13.2 micrograms/mL, at 37 deg C in a humidified atmosphere of 5% $CO_2$ and 95% air over night.

After transfection, the medium was replaced with D-MEM/F12/5% FCS supplemented with 0.6 mg/ml G418, and a selective culture was carried out at 37 deg C in a humidified atmosphere of 5% $CO_2$ and 95% air. Cells that had grown in the medium for selective culture were subjected to several successive rounds of subculture in the medium to give recombinant cells.

Then, according to the limiting dilution technique, the recombinant cells were seeded on a 96-well plate in such a manner that not more than one cell might be seeded per well, and the cells were cultured for about 10 days to let each of them form a monoclonal colony. The culture supernatant in the wells where a monoclonal colony was formed were sampled and examined for human I2S activity as described in Example 6 below but without desalting procedure, and cell lines which were found expressing a high activity for I2S were selected.

For adaptation to serum-free suspension cell culture, the selected cell lines were cultured in a commercially available serum-free medium, IS CHO-V-GS medium (Irvine Scientific) supplemented with 8 mM L-glutamine, 120 mg/L G148, at 37 deg C in a humidified atmosphere of 5% $CO_2$ and 95% air until the cells stably grew. The cells then were suspended in IS CHO-V-GS medium (Irvine Scientific) supplemented with 8 mM L-glutamine, 100 micromoles/L of hypoxanthine, 16 micromoles/L of thymidine, 120 mg/L G148, and 10% DMSO, and stored as seed cells in liquid nitrogen.

Example 3

3. Culture of Recombinant Cells for Expression of Human I2S

The above seed cells were thawed and diluted to a cell density of $4 \times 10^5$ cells/mL and cultured for 3 to 4 days in IS CHO-V-GS medium supplemented with 8 mM of L-glutamine, 100 micromoles/L of hypoxanthine, 16 micromoles/L of thymidine (IS medium), and then diluted to a cell density of $2 \times 10^5$ cells/mL with IS medium and cultured for 3 to 4 days. The cells were again diluted to a cell density of $2 \times 10^5$ cells/mL and subjected to expansion culture which was performed by static-culture for 4 days at 37 deg C in a humidified atmosphere of 5% $CO_2$ and 95% air.

The number of the cells was counted, and the cell culture was diluted with IS medium to a cell density of $5 \times 10^5$ cells/mL. 10 mL of CDLC (Chemically defined Lipid Concentrate, Invitrogen) was added to 1 L of the diluted culture and then the cells were shake-cultured for 3 days. The culture conditions for this were as follows: shaking speed: 20 rpm, pH 7.2, dissolved oxygen: 70%, temperature: 37 deg C. The scale of culture was escalated until the culture volume had reached 160 L.

Then the number of the cells was counted, and the cells were diluted to a cell density of $2 \times 10^5$ cells/mL with EX-CELL™ 302 serum free-medium (EX medium, SAFC Bioscience) supplemented with 4 mM of L-glutamine, 100 micromoles/L of hypoxanthine, 16 micromoles/L of thymidine. 720 L of the diluted culture was transferred to an incubation tank and cultured for 7 days. The culture conditions for this were as follows: agitation speed: about 90 rpm, pH 7.0, dissolved oxygen: 50%, temperature: 37 deg C. 63 L of EX-CELL™ 302 serum free-medium supplemented with 3.6 mol of L-glutamine and 10 g of human insulin was added on the 3rd and the 5th days. Sampling was made every day during the culture, and measurement was performed for cell number, survival rate, glucose concentration, lactic acid concentration, and amount of expressed human I2S. In the case where glucose concentration became lower than 9.5 mmol/L, glucose solution was added so that the concentration reached 19 mmol/L.

Figures 1, 2:
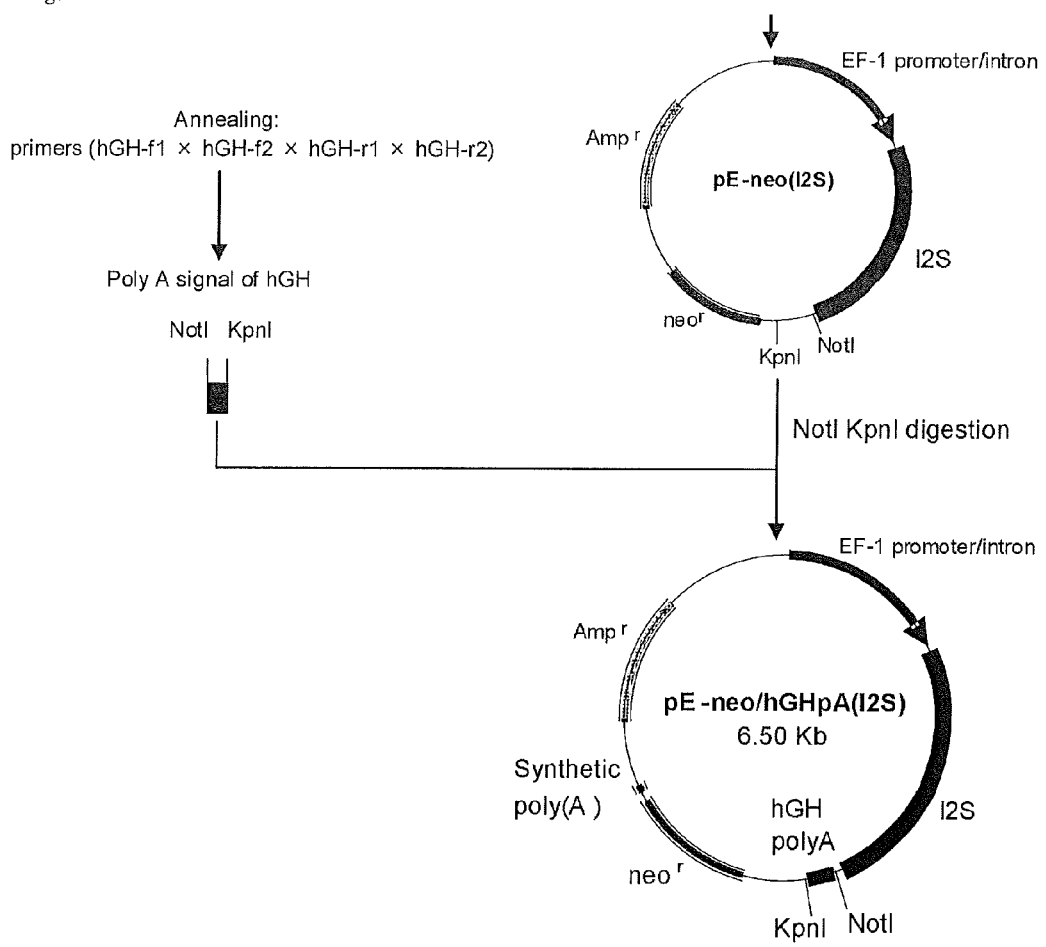
Figure 2:
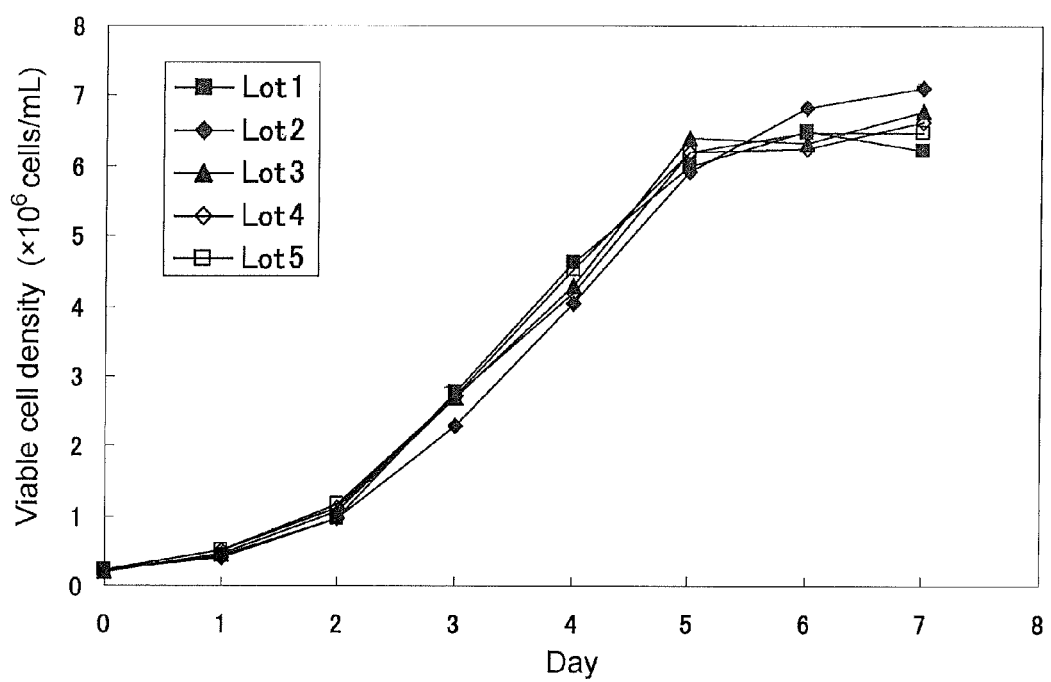

The above-mentioned cell culture was repeated 6 times (Lot Nos. 1-6). In each culture, viable cell density reached about $1 \times 10^7$ cells/mL or more on days 6-7 of culture, indicating that high-density cell culture was successfully achieved (FIG. 2). The concentration of rhI2S (the 26th to 550th amino acids of SEQ ID NO: 10) in the medium secreted by the cells was measured by ELISA and compared to the cell density, which revealed that the concentration increased with a slight time lag (data not shown).

The cell culture was collected and filtered through Millistak+ HC Pod Filter grade DOHC, (Millipore), and then through Millistak+ HC grade A1HC (Millipore), to give a culture supernatant.

Example 4

4. Method for Purification of rhI2S (the 26th to 550th Amino Acids of SEQ ID NO: 10)

To the culture supernatant collected above was added acetic acid to adjust the pH of the culture supernatant to 4.3. A precipitate formed by this was removed by filtration through Millistak+HC Pod Filter grade DOHC (Millipore) and then through Opticap XL4 Durapore (Millipore). Culture supernatant thus recovered was loaded on a Capto MMC column (column volume: 6.3 L, bed height: about 20 cm, GE Healthcare), a cation-exchange column having a selectivity based both on hydrophobic interaction and on hydrogen bond formation, which had been equilibrated with a threefold column volume of 20 mM acetate buffer (pH 4.3) containing 150 mM NaCl. This buffer then was supplied to the column at a linear flow rate of 150 cm/hr to let rhI2S (the 26th to 550th amino acids of SEQ ID NO: 10) be adsorbed by the column. Then after the column was washed with a fourfold column volume of the same buffer supplied at the same flow rate, the adsorbed rhI2S (the 26th to 550th amino acids of SEQ ID NO: 10) was eluted with a fourfold column volume of 20 mM acetate buffer (pH 5.1) containing 150 mM NaCl.

Then, the eluate from the above Capto MMC column was diluted 1.5 times with water, and the pH of this diluted solution was adjusted to 5.0. This solution then was loaded on a Blue sepharose 6FF column (column volume: about 7.1 L, bed height: about 10 cm, GE Healthcare), a dye affinity column, which had been equilibrated with a fourfold column volume of 20 mM acetate buffer (pH 5.0) containing 100 mM NaCl. This buffer then was supplied to the column at a linear flow rate of 50 cm/hr to let rhI2S (the 26th to 550th amino acids of SEQ ID NO: 10) be adsorbed by the column. Then, the column was washed with a fourfold column volume of the same buffer supplied at the same flow rate, and the adsorbed rhI2S (the 26th to 550th amino acids of SEQ ID NO: 10) then was eluted with a fivefold column volume of 20 mM phosphate buffer (pH 6.0) containing 150 mM NaCl.

Then, as a virus inactivation process, tri-n-butyl phosphate (TNBP) and polysorbate 80 were added to rhI2S (the 26th to 550th amino acids of SEQ ID NO: 10)-containing fractions of the eluate from the above Blue sepharose 6FF column so that their final concentrations would be 0.3%(v/v) and 1%(w/v), respectively, and this mixture solution then was gently stirred for 3 hours at room temperature. The solution then was filtered through Opticap XL4 Durapore (Millipore).

To the above solution, virus-inactivated, was added diluted hydrochloric acid to adjust its pH to 5.5. This solution then was loaded on a Q Sepharose Fast Flow column (column volume: about 6.3 L, bed height: about 20 cm, GE Healthcare), an anion-exchange column, which had been equilibrated with a fourfold column volume of 20 mM phosphate buffer (pH 5.5) containing 150 mM NaCl. This buffer then was supplied to the column at a linear flow rate of 150 cm/hr to let rhI2S (the 26th to 550th amino acids of SEQ ID NO: 10) be adsorbed by the column. Then, the column was washed with a fourfold column volume of the same buffer supplied at the same flow rate, and the adsorbed rhI2S (the 26th to 550th amino acids of SEQ ID NO: 10) then was eluted with a fourfold column volume of 20 mM phosphate buffer (pH 5.5) containing 400 mM NaCl.

Then, the eluate from the above Q Sepharose Fast Flow column was diluted about 2.7 times with 400 mM NaCl solution, and then the pH of this diluted solution was adjusted to 6.5. This solution then was loaded on a CFT Type II 40 micrometer column (column volume: about 3.2 L, bed height: about 10 cm, Bio-Rad), a fluoroapatite column, which had been equilibrated with a ninefold column volume of 7.5 mM phosphate buffer (pH 6.5) containing 400 mM NaCl. This buffer then was supplied at a linear flow rate of 150 cm/hr to let rhI2S (the 26th to 550th amino acids of SEQ ID NO: 10) be adsorbed by the column. After the column was washed with a fifteen-fold column volume of the same buffer supplied at the same flow rate, the adsorbed rhI2S (the 26th to 550th amino acids of SEQ ID NO: 10) then was eluted with a fifteen-fold column volume of 150 mM phosphate buffer (pH 6.5) containing 150 mM KCl.

Then, the eluate from the above CFT Type II 40 micrometer column was concentrated using Biomax™ 30 membrane (Millipore). About 1.2 L of this concentrated solution was loaded on a Superdex 200 prep grade column (column volume: about 19 L, bed height: about 64 cm, GE Healthcare) which had been equilibrated with 20 mM phosphate buffer (pH 6.0) containing 137 mM NaCl and 0.02%(w/v) polysorbate 80. The same buffer then was supplied at a linear flow rate of 14.9 cm/hr, and fractions which exhibited peak absorption at 280 nm were collected as fractions containing purified rhI2S (the 26th to 550th amino acids of SEQ ID NO: 10).

The fractions containing purified rhI2S (the 26th to 550th amino acids of SEQ ID NO: 10) were combined and filtered through Planova™ 15N (0.3 m$^2$ size, Asahi Kasei Medical) and then through Millipak-20 Filter Unit 0.22 micrometer to avoid any possible viral contamination in the final product.

The amount of rhI2S (the 26th to 550th amino acids of SEQ ID NO: 10) after each step was quantified using ELISA method described below. The recovery rate of rhI2S (the 26th to 550th amino acids of SEQ ID NO: 10) of each purification step is shown in Table 1, in which "rhI2S (the 26th to 550th amino acids of SEQ ID NO: 10) recovery rate/step" means the proportion of the amount of recovered rhI2S (the 26th to 550th amino acids of SEQ ID NO: 10) to that of loaded rhI2S (the 26th to 550th amino acids of SEQ ID NO: 10) in each step, and "rhI2S (the 26th to 550th amino acids of SEQ ID NO: 10) recovery rate/total" the proportion of the amount of recovered rhI2S (the 26th to 550th amino acids of SEQ ID NO: 10) in each process to the initial amount of rhI2S (the 26th to 550th amino acids of SEQ ID NO: 10) subjected to the purification process. The amount of rhI2S (the 26th to 550th amino acids of SEQ ID NO: 10) subjected to the above purification process was 14435.2 mg, of which 9086.3 mg of rhI2S (the 26th to 550th amino acids of SEQ ID NO: 10) was finally recovered, thus giving the rhI2S (the 26th to 550th amino acids of SEQ ID NO: 10) recovery rate/total as high as 62.9%. These results show that the method for purification described above enables to purify rhI2S (the 26th to 550th amino acids of SEQ ID NO: 10) in very high yield and in a large production scale.

[Table 1]

TABLE 1

Recovery rate of rhI2S in each purification step (Lot No. 1)

| Purification process | rhI2S loaded (mg) | rhI2S recovered (mg) | rhI2S recovery rate/step (%) | rhI2S recovery rate/total (%) |
|---|---|---|---|---|
| Cation-exchange column (Capto MMC) | 14435.2 | 12800.2 | 88.7 | 88.7 |
| Dye affinity column (Blue Sepharose 6FF) | 13436.0 | 9155.4 | 68.1 | 63.4 |
| Anion-exchange column (Q Sepharose FF) | 12885.5 | 12356.5 | 95.9 | 85.6 |
| Fluoroapatite column (CFT TypeII) | 11719.9 | 7882.3 | 67.3 | 54.6 |
| Gel filtration column (Superdex 200 pg) | 8905.5 | 9086.3 | 102.0 | 62.9 |

Example 5

5. Analysis of Human I2S by ELISA

To each well of a 96-well microtiter plate (Nunc) was added 100 microliters of mouse anti-human monoclonal antibody diluted to 4 micrograms/mL with 0.05 M Carbonate-Bicarbonate buffer (pH 9.6), and the plate was let stand for at least 1 hour at room temperature to let the antibody be absorbed by the wells. Then, after each well was washed three times with phosphate buffered saline (pH 7.4) containing 0.05% Tween 20 (PBS-T), 200 microliters of Starting Block (PBS) Blocking Buffer (Thermo Fisher Scientific) was added to the well, and the plate was let stand for at least 30 minutes at room temperature. Then, after each well was washed three times with PBS-T, 100 microliters of the test sample or human I2S standard, which had been diluted as desired with PBS containing 0.5% BSA and 0.05% Tween 20 (PBS-BT), was added to the well, and the plate was let stand for at least one hour at room temperature. Then, after each well was washed three times with PBS-T, 100 microliters of biotin-labeled anti-human I2S monoclonal antibody diluted with PBS-BT was added and the plate was let stand for at least 1 hour. Then, after each well was washed three times with PBS-T, 100 microliters of streptavidin-HRP (R&D SYSTEMS) diluted with PBS-BT was added and the plate was let stand for at least 30 minutes. Then, after each well was washed three times with PBS-T, 100 microliters of 0.4 mg/mL o-phenylendiamine with phosphate-citrate buffer (pH 5.0) was added to the well, and the plate was stand for 8 to 20 minutes at room temperature. Then 0.1 mL of 1 mol/L $H_2SO_4$ was added to each well to stop the reaction, and the optical density at 490 nm was measured for the well on a 96-well plate reader.

Example 6

6. Measurement of the Activity of rhI2S (the 26th to 550th Amino Acids of SEQ ID NO: 10)

Samples were desalted by membrane filtration using vertical polyethersulfone membrane (VIVASPIN 2 5,000 MWCO PES; Sartorius) as ultrafilter membrane, and then desalted samples were diluted to approximately 100 ng/mL with Reaction Buffer (5 mM sodium acetate, 0.5 mg/L BSA, 0.1% Triton X-100, pH 4.45). To each well of a 96-well microtiter plate (FluoroNunc Plate, Nunc) 10 microliters of each rhI2S (the 26th to 550th amino acids of SEQ ID NO: 10) sample was added and pre-incubated for 15 minutes at 37 deg C. Substrate solution was prepared by dissolving 4-methylumbelliferyl sulfate (SIGMA) in Substrate Buffer (5 mM sodium acetate, 0.5 mg/mL BSA, pH 4.45) to a final concentration of 1.5 mg/mL. 100 microliters of Substrate solution was added to each well containing rhI2S (the 26th to 550th amino acids of SEQ ID NO: 10) sample and the plate was let stand for 1 hour at 37 deg. C in the dark. After the incubation, 190 microliters of Stop Buffer (0.33 M glycine, 0.21 M sodium carbonate, pH 10.7) was added to each well containing the sample. 150 microliters of 0.4 micromole/L 4-methylumbelliferone (4-MUF, Sigma) solution and 150 microliters of Stop Buffer was added to a well as the standard, then the plate was read on a 96-well plate reader with excitation light at the wavelength of 330 nm and fluorescent light at the wavelength of 440 nm.

A standard curve was produced by measuring fluorescence intensity at various concentrations of 4-MUF in solution. The fluorescence intensity of each sample was extrapolated to the standard curve. Results were calculated as activity in Units/mL where one Unit of activity was equal to 1 micromole of 4-MUF produced per minute at 37 deg. C. A published US patent application (publication No. 2004-0229250) was referred to for conducting this measurement. The specific activity of human I2S purified above was found to be about 2630 mU/mg.

Example 7

7. Measurement of Host Cell Proteins

A rabbit was immunized with proteins obtained from CHO cells (host cell proteins: HCPs), then antiserum was prepared from blood of the rabbit. Total IgG was purified from the antiserum by protein A column chromatography, then the antibody against HCPs (rabbit anti-HCP antibody) was purified from the total IgG by affinity column chromatography containing HCP-coupled resin. Biotin-labeled rabbit anti-HCP antibody was prepared by conjugating rabbit anti-HCP antibody to biotin moiety using EZ-Link Sulfo-NHS-LC-Biotinylation Kit (Thermo).

One hundred microliters of Rabbit anti-HCP antibody diluted to 5 micrograms/mL with 100 mM sodium carbonate buffer (pH 9.6) was added to each well of a 96-well microtiter plate (Nunc). After the plate was let stand for at least 1 hour at room temperature to allow the antibody to be adsorbed, each well was washed three times with T-TBS (Tris buffered saline with 0.05% Tween 20, pH 8.0, SIGMA), then 200 microliters of Super Block Blocking Buffer in TBS (Thermo) was added to each well, and the plate was let stand for at least 30 minutes at room temperature. Then each well was washed three times with T-TBS, then 100 microliters of sample solution diluted with Super Block Blocking Buffer in TBS (Thermo) was added, and the plate was rotated mildly for at least 1 hour at room temperature. After each well was washed three times with T-TBS, 100 microliters of 60 ng/mL biotin-labeled rabbit anti-HCP antibody in Super Block Blocking Buffer in TBS (Thermo) was added, and the plate was rotated mildly for at least 1 hour at room temperature. Then each well was washed three times with T-TBS, and following addition of 100 microliters of horseradish peroxidase-labeled streptavidin (NeutrAvidin, Horseradish Peroxidase Conjugated, Thermo) diluted with Super Block Blocking Buffer in TBS (Thermo), the plate was rotated mildly for at least 30 minutes at room temperature. Each well then was washed three times with T-TBS, and after addition of 100 microliters of TMB solution (TMB Peroxidase Substrate, KPL), the plate was let stand for 15 to 30 minutes at room temperature. To each well was added 100 microliters of 1 M phosphoric acid to stop the reaction, and the optical density at 450 nm was measured for each well on a 96-well plate reader. As a result, the calculated concentration of HCPs in the rhI2S (the 26th to 550th amino acids of SEQ ID NO: 10) purified above (Lot No. 1) was only 12 ppm, which is the level acceptable for using this rhI2S (the 26th to 550th amino acids of SEQ ID NO: 10) as a medicament injectable to human body.

Example 8

8. Analysis of Purity of rhI2S (the 26th to 550th Amino Acids of SEQ ID NO: 10)

Figure 3:
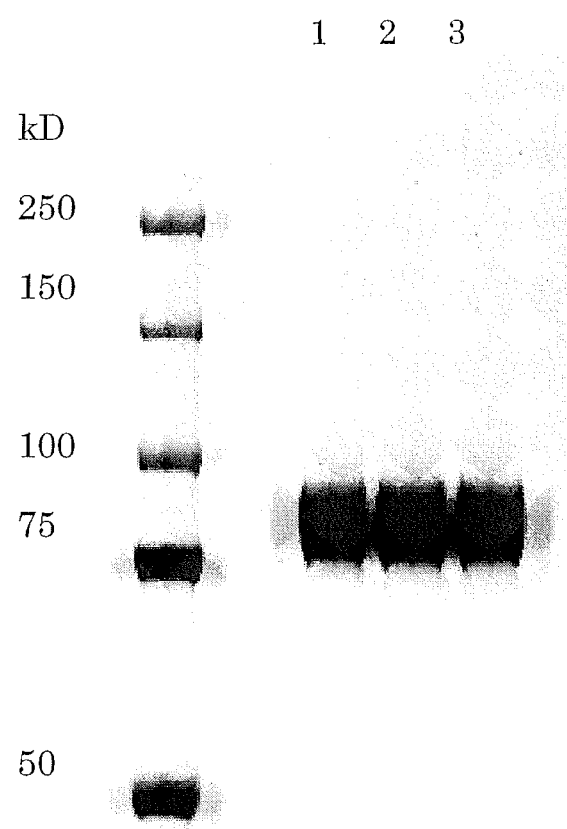
FIG. 3 shows the pattern obtained by SDS-PAGE electrophoresis of purified rhI2S (the 26th to 550th amino acids of SEQ ID NO: 10). To lanes 1 to 3 was applied 2.5 micrograms of the purified rhI2S (the 26th to 550th amino acids of SEQ ID NO: 10) of Lot Nos. 1 to 3, respectively.

The rhI2S (the 26th to 550th amino acids of SEQ ID NO: 10) purified above was subjected to SDS-PAGE electrophoresis under non-reductive, heating condition. The gel-stained with Coomassie brilliant blue revealed a single band at the position of molecular weight of about 80 kD, which corresponds to the molecular weight of rhI2S (the 26th to 550th amino acids of SEQ ID NO: 10) reported previously (U.S. Pat. No. 5,932,211) (FIG. 3).

Further, rhI2S (the 26th to 550th amino acids of SEQ ID NO: 10) purified above was analyzed by Size-elimination HPLC (SE-HPLC) and SAX-HPLC. HPLC was performed using LC-20A System, SPD-20AV UV/VIS Detector (Shimazu Corp.).

For SE-HPLC analysis, 10 microliters of sample solution containing 2 mg/mL of rhI2S (the 26th to 550th amino acids of SEQ ID NO: 10) purified above was applied onto TSK gel G3000SW$_{XL}$ column (7.8 mm I.D.×30 cm, TOSOH) equilibrated with 25 mM phosphate buffered saline (PBS) at a flow rate of 0.5 ml/min. Elution profile was produced by monitoring absorbance at 215 nm. For SAX-HPLC analysis, 20 microliters of a sample solution containing 2 mg/mL of rhI2S (the 26th to 550th amino acids of SEQ ID NO: 10) was applied onto TSK gel Q-STAT column (4.6 mm I.D.×10 cm, TOSOH) equilibrated with 10 mM Tris-HCl (pH 7.5) at a flow rate of 1.0 ml/min. NaCl concentration in this mobile phase buffer was increased up to 0.5 M at 30 min after injection with linear slope. Elution profile was produced by monitoring absorbance at 280 nm.

Figure 4:
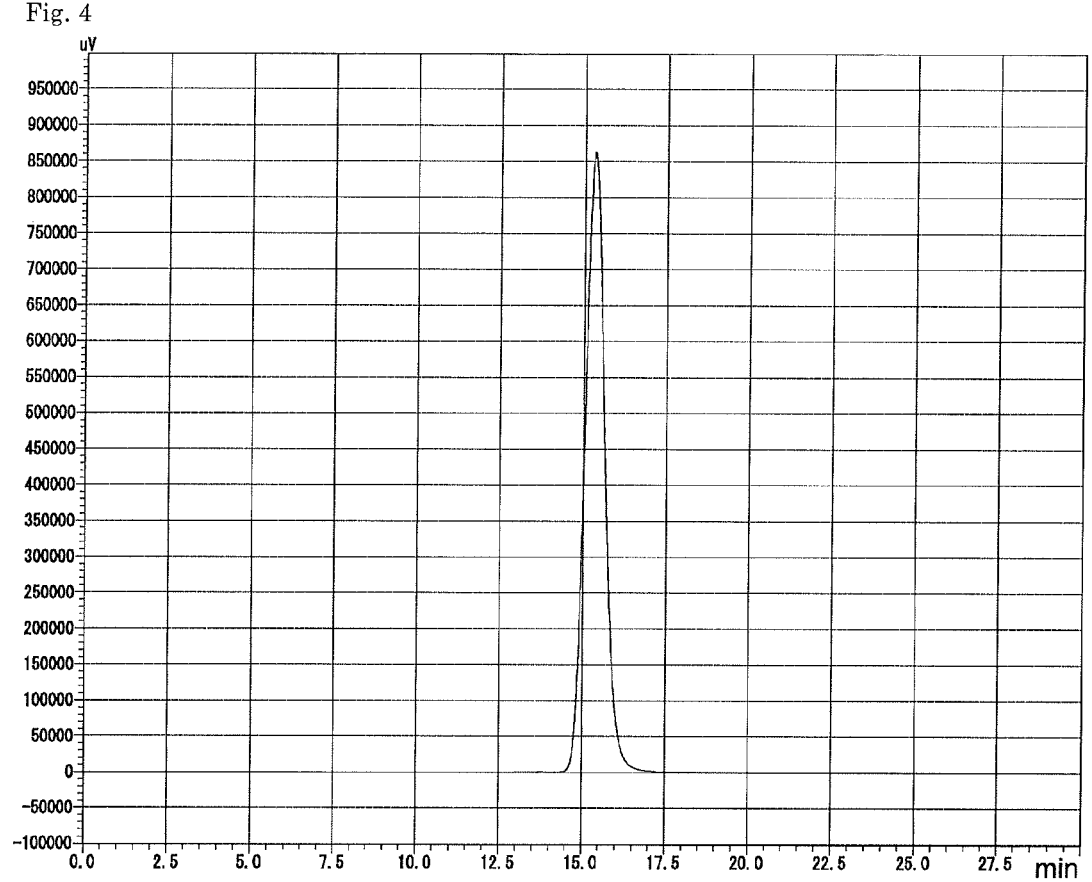
FIG. 4 shows the SE-HPLC chart of the purified rhI2S (the 26th to 550th amino acids of SEQ ID NO: 10) (Lot No. 1). The vertical and horizontal axes show absorbance at 215 nm and retention time, respectively.
Figure 5:
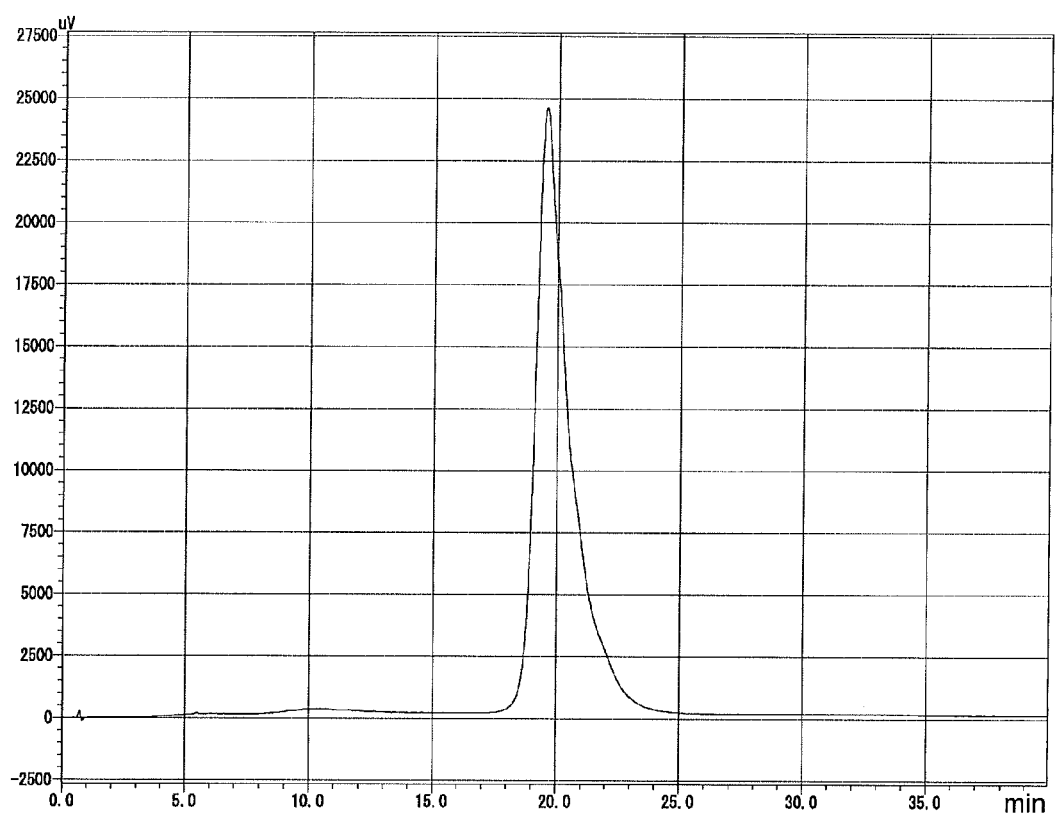
FIG. 5 shows the SAX-HPLC chart of the purified rhI2S (the 26th to 550th amino acids of SEQ ID NO: 10) (Lot No. 1). The vertical and horizontal axes show absorbance at 280 nm and retention time, respectively.

Both of SE-HPLC and SAX-HPLC of the above purified rhI2S (the 26th to 550th amino acids of SEQ ID NO: 10) revealed a single peak alone (FIGS. 4 and 5, respectively). These data showed that the rhI2S (the 26th to 550th amino acids of SEQ ID NO: 10) obtained above was highly purified and free of any detectable contaminants. Furthermore, the concentration of host cell proteins (HCPs) contaminating the purified rhI2S (the 26th to 550th amino acids of SEQ ID NO: 10) was only 12 ppm as measured by ELISA. Taken together, the data shown above demonstrate that the rhI2S (the 26th to 550th amino acids of SEQ ID NO: 10) purified above is such a high purity as may be directly used as a medical drug.

Example 9

9. Measurement of Cellular Uptake of rhI2S (the 26th to 550th Amino Acids of SEQ ID NO: 10) Using Normal Human Fibroblast Cultured human fibroblasts (CCD-1076SK, purchased from DS Pharma Biomedical Co., Ltd.) were suspended in MEM-Eagle's medium (Gibco) containing 10% heat-inactivated FBS and 2 mM L-glutamine, and the cell density was adjusted to $8.0 \times 10^4$ cells/mL. One hundred microliters of cell suspension was seeded into each well of a 96-well microplate and cultured for 2 days at 37 deg C in a humidified atmosphere of 5% $CO_2$ and 95% air. Samples containing the present rhI2S (the 26th to 550th amino acids of SEQ ID NO: 10) obtained above (Lot No. 1) or a commercially-available medicinal rhI2S (the 26th to 550th amino acids of SEQ ID NO: 10) were serially diluted with the medium to make various concentrations of from 4.88 ng/mL to 20 micrograms/mL. Then, the medium in the 96-well microplate where fibroblasts had been seeded was removed with a micropipette, and 100 microliters of each sample diluted above was added in duplicate manner to the wells, and incubation was done for 18 hrs. The final concentrations of rhI2S (the 26th to 550th amino acids of SEQ ID NO: 10) in the incubation was 4.88 ng/mL to 20 micrograms/mL. To confirm the specific binding of rhI2S (the 26th to 550th amino acids of SEQ ID NO: 10) to mannose 6-phosphate (M6P) receptor in this assay, samples containing 10 mmol/L of mannose 6-phosphate (M6P) as an antagonist and 20 micrograms/mL of rhI2S (the 26th to 550th amino acids of SEQ ID NO: 10) were prepared and added to the 96-well microplate, and incubated was done in the same manner as described above. The assay was made in triplicated manner.

After washed with ice cold PBS thrice, cells were lysed with M-PER Mammalian Protein Extraction Reagent (Thermo scientific) supplemented with 0.5% protease inhibitor cocktail (Sigma). Then the amount of total cellular protein was measured by Pierce BCA™ Protein Assay kit (Pierce, Ill., USA), and the amount of rhI2S (the 26th to 550th amino acids of SEQ ID NO: 10) taken up in the cells was determined by ELISA method as described above. The amount of rhI2S (the 26th to 550th amino acids of SEQ ID NO: 10) taken up was calculated per unit mass (mg) of the amount of total cellular protein, and plotted on a graph (FIG. 6).

Figure 6:
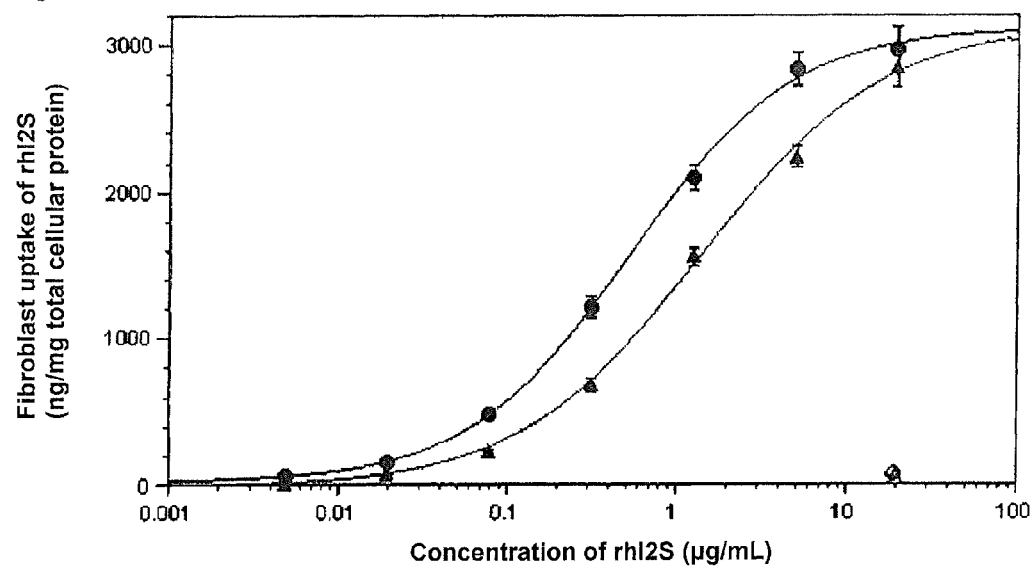
FIG. 6 shows the result of the measurement of fibroblast uptake of rhI2S (the 26th to 550th amino acids of SEQ ID NO: 10) (Lot No. 1) and a commercially-available medicinal rhI2S (the 26th to 550th amino acids of SEQ ID NO: 10). The vertical axis shows the amount (ng) of rhI2S (the 26th to 550th amino acids of SEQ ID NO: 10) taken up per unit mass (mg) of the total cellular protein (ng/mg total cellular protein). Horizontal axis shows the concentration of rhI2S (the 26th to 550th amino acids of SEQ ID NO: 10) in the culture medium. Filled circles and filled triangles indicate the values of fibroblast uptake of rhI2S (the 26th to 550th amino acids of SEQ ID NO: 10) (Lot No. 1) and a commercially available medicinal rhI2S (the 26th to 550th amino acids of SEQ ID NO: 10), respectively. An open circle and a filled triangle close to the horizontal axis indicate the value of fibroblast uptake of rhI2S (the 26th to 550th amino acids of SEQ ID NO: 10) (Lot No. 1) and commercially-available medicinal rhI2S (the 26th to 550th amino acids of SEQ ID NO: 10) in the presence of 20 mmol/L M6P, respectively.

The result showed that the present rhI2S (the 26th to 550th amino acids of SEQ ID NO: 10) (Lot No. 1) was taken up by cultured human fibroblasts in a dose-dependent manner more efficiently than the commercially-available medicinal rhI2S (the 26th to 550th amino acids of SEQ ID NO: 10) (FIG. 6). The $EC_{50}$ of cellular uptake of the present rhI2S (the 26th to 550th amino acids of SEQ ID NO: 10) (Lot No. 1) and the commercially-available medicinal rhI2S (the 26th to 550th amino acids of SEQ ID NO: 10) was 0.452+/−0.0853 and 1.455+/−0.434 micrograms/mL (Mean+/−s.d.), respectively. Addition of M6P to the culture at the concentration of 10 mmol/L inhibited the cellular uptake of both of the present rhI2S (the 26th to 550th amino acids of SEQ ID NO: 10) (Lot No. 1) and the commercially-available medicinal rhI2S (the 26th to 550th amino acids of SEQ ID NO: 10) almost completely, indicating that they were taken up by cultured human fibroblasts through its specific binding to the M6P receptor. Non-patent document (Tsukimura T. et. al., Biol Pharm Bull. 31: 1691-5, 1979) was referred to for conducting the above measurement. These results show that both of the present rhI2S (the 26th to 550th amino acids of SEQ ID NO: 10) (Lot No. 1) and the commercially-available medicinal rhI2S (the 26th to 550th amino acids of SEQ ID NO: 10) contain one or more M6P residues in its oligosaccharide chain.

Example 10

10. Measurement of Affinity of rhI2S (the 26th to 550th Amino Acids of SEQ ID NO: 10) to M6P Receptor Binding affinity of rhI2S (the 26th to 550th amino acids of SEQ ID NO: 10) for the M6P receptor was measured by the method described below.

Plasmid containing cDNA encoding human mannose-6-phosphate receptor (human M6P receptor), which is essential for M6P binding, was obtained from ATCC (ATCC No. 95660). A DNA fragment encoding the domain 9 of human M6P receptor (hMPR9) was amplified from the plasmid by PCR using a set of primers:

```
(a) hMPR9-f:
                                    (SEQ ID NO: 11)
5'-ATAATCCATGGTTGTCAGAGTGGAAGGGGAC-3',
and (b) hMPR9-r:
                                    (SEQ ID NO: 12)
5'-GCAATGCGGCCGCGAAAGGTGGGCAGGCATAC-3'.
```

The amplified DNA fragment was digested with NcoI and NotI, and inserted into the NcoI-NotI site of pET26 vector (Novagen). The resultant plasmid was designated pET26-MPR9. Two-step PCR reaction was conducted using two sets of primers, which resulted in the amplification of a DNA fragment shown as SEQ ID NO:13, which encoded hMPR9 containing additional sequences at both of its 5'- and 3'-termini. As this amplified DNA fragment encodes hMPR9 having Bip signal at its N-terminus and His-tag at its C-terminus, it was designated Bip-tagged-hMPR9.

The first reaction of the 2-step PCR reaction above was conducted using pET26-MPR9 as template and a set of primers:

```
(c) MPR9-f2:
                               (SEQ ID SEQ ID NO: 14)
5'-GTTGGCCTCTCGCTCGGGAGCGCTGTTGTCAGAGTGGAAGG

GGAC-3',
and (d) MPR9-r2:
                                    (SEQ ID NO: 15)
5'-ATAATGCGGCCGCTCAGTGATGGTGATGGTGATGTGGCGCG

CCGGATCCGAAAGGTGGGCAGGCATAC-3'.
```

Subsequently, using the amplified DNA fragment as template, the second PCR was conducted using a set of primers:

```
(e) MPR9-f3:
                                    (SEQ ID NO: 16)
5'-ATAATCCATGGGATATCTAATAAATATGAAGTTATGCATATTAC

TGGCCGTCGTCGCCTTTGTTGGCCTCTCG-3',
and (f) MPR9-r3:
                                    (SEQ ID NO: 17)
5'-ATAATGCGGCCGCTCAGTGATGGTGATGGTGATGTGGCGCGCCG

GATCCGAAAGGTGGGCAGGCATAC-3'.
```

Then the resultant DNA fragment was digested with EcoRV and NotI, and ligated into the Eco47III-NotI site of the pIB/V5-His-DEST vector (Invitrogen). The resultant plasmid was designated pXBi-MPR9, with which High Five cells were transfected to obtain cells expressing His-tagged-hMPR9 which was derived from Bip-tagged hMPR9 through removal of Bip signal sequence.

High Five cells (Invitrogen) were grown in 24-well plate until 50% confluent using Express Five medium (Invitrogen) and transfected with the pXBi-MPR9 using the Hily Max transfection reagent (Dojin chemical, Japan). The cells were cultured in the presence of 30 micrograms/mL blasticidin to select stable transfectant. Stably transfected cells then were expanded and cultured in the Erlenmeyer flask (100 mL) for 4 days. The culture then was harvested and centrifuged at 3,000 rpm for 30 min, and the supernatant was collected. The supernatant was filtrated though 0.22 micrometer filter (Millapore), then diluted 5-fold with equilibration buffer (10 mM phosphate buffer containing 300 mM NaCl (pH 7.2)). The diluted supernatant was applied to the chromatography column with Profinity IMAC Ni-charged Resin (bed volume: 1 mL, Bio-Rad) equilibrated with an equilibration buffer, then the column was washed with 5 bed volumes of the equilibration buffer. Then the His-tagged-hMPR9 bound to the resin was eluted by applying to the column 5 bed volumes of 10 mM NaPO4, 300 mM NaCl and 10 mM imidazole (pH 7.2), and subsequently 5 bed volumes of 10 mM NaPO4, 300 mM NaCl and 300 mM imidazole (pH 7.2). Fractions containing His-tagged-hMPR9 were collected and concentrated by Amicon 3K (Millipore) with the buffer exchanged to 20 mM Tris buffer containing 150 mM NaCl (pH 7.4). The concentration of the His-tagged-hMPR9 was determined by measuring absorbance at 280 nm.

Binding affinity of rhI2S (the 26th to 550th amino acids of SEQ ID NO: 10) for M6PR was measured using Biacore T100 (GE Healthcare) equipped with a nitrilotriacetic acid-fixed sensor chip (Series S Sensor Chip NTA "BR-1005-32"). Biacore T100 is a measuring apparatus based on surface plasmon resonance (SPR), where a sample containing a ligand is sent at a constant flow rate onto the surface of the sensor chip on which receptor is fixed. If the ligand binds to the receptor, the mass of the surface sensor chip is increased due to the mass of the ligand bound to the receptor, and a shift of the SPR signal can be detected as a change in the resonance unit (RU) in proportion to the amount of bound ligand. In general, for proteins, 1 RU is approximately 1 pg/mm$^2$. To activate the sensor chip, 10 mM HEPES (pH 7.4) containing 500 micromoles/L NiCl$_2$, 150 mM NaCl, 50 micromoles/L EDTA and 0.05% Surfactant P20 was loaded at the flow rate of 10 microliters/min for 60 sec. Then, approximately 50-100 RU of the His-tagged-hMPR9 purified above was applied, and subsequently 10 mM HEPES (pH 7.4) containing 150 mM NaCl, 50 micromoles/L EDTA and 0.05% Surfactant P20 was loaded at the flow rate of 10 microliters/min for 60 sec to fix the tagged-hMPR9 on the activated sensor chip. Each sample was diluted to the concentrations of rhI2S (the 26th to 550th amino acids of SEQ ID NO: 10) of 12.5, 6.25, 3.125 and 1.5625 nmol/L with 10 mM HEPES (pH 7.4) containing 150 mM NaCl, 50 micromoles/L EDTA and 0.05% Surfactant P20, and each of the dilutions prepared was applied at a flow rate of 50 microliters/min for 300 sec to let rhI2S (the 26th to 550th amino acids of SEQ ID NO: 10) bind to the His-tagged-hMPR9 on the sensor chip. Then, 10 mM HEPES (pH 7.4) containing 150 mM NaCl, 50 micromoles/L EDTA and 0.05% Surfactant P20 was run at a flow rate of 50 microliters/min for 180 sec while constantly monitoring the dissociation status between the His-tagged-hMPR9 and rhI2S (the 26th to 550th amino acids of SEQ ID NO: 10). Subsequently 10 mM HEPES (pH 8.3) containing 150 mM NaCl, 350 mM EDTA, and 0.05% Surfactant P20 was run at a flow rate of 50 microliters/min for 60 sec to regenerate the sensor chip. The dissociation constant (Kd) was automatically calculated from the dissociation status monitored above by Biacore T100 Evaluation Software.

The Kd value (dissociation constant) for the present rhI2S (the 26th to 550th amino acids of SEQ ID NO: 10) obtained by the above method (Lot No. 1 to 7) ranged from 7.58 to 12.29×10$^{-10}$ mol/L, which averaged to 10.4×10$^{-10}$ mol/L, whereas the Kd value for the commercially-available medicinal rhI2S (the 26th to 550th amino acids of SEQ ID NO: 10) was $33.2 \times 10^{-10}$ mol/L (See Table 2). The result showed that the present rhI2S (the 26th to 550th amino acids of SEQ ID NO: 10) obtained by the above method bound to the M6P receptor more efficiently than the commercially-available medicinal rhI2S (the 26th to 550th amino acids of SEQ ID NO: 10), and suggested that highly efficient cellular uptake of the present rhI2S (the 26th to 550th amino acids of SEQ ID NO: 10) (Lot No. 1) shown in FIG. 6 was caused by the stronger affinity of the present rhI2S (the 26th to 550th amino acids of SEQ ID NO: 10) for the M6P receptor.

TABLE 2

Kd values and mannose-6-phosphate content

| | rhI2S of present invention | | Commercially available rhI2S |
|---|---|---|---|
| | Lot. Nos. 1-7 | Average (Lot Nos. 1-7) | |
| Kd [×10⁻¹⁰ mol/L] | 7.58-12.29 | 10.4 | 33.2 |
| M6P content [mol/mol] | 3.74-5.38 | 4.37 | 3.39 |

Example 11

11. Measurement of M6P Content

Number of M6P residue in oligosaccharide chain of rhI2S (the 26th to 550th amino acids of SEQ ID NO: 10) was measured by the method described below. Standard solution was prepared by dissolving D-mannose-6-phosphate, D(+)-mannose, L(−)-fucose, and D(+)-galactose with water at the concentration of 0.1 mg/mL, 0.1 mg/mL, 0.036 mg/mL and 0.1 mg/mL, respectively. Mobile phase A was prepared by dissolving 6.2 g of boric acid in water, adjusting the pH to 9.0 with 2M NaOH, and then adding water to make a total volume of 1000 mL. Mobile phase B was prepared by dissolving 6.2 g of boric acid and 11.7 g of NaCl in water, adjusting pH to 9.0 with 2M NaOH, and then adding water to make a total volume of 1000 mL. Reaction buffer was prepared by dissolving 10 g of L-arginine and 30 g of boric acid in water to a total volume of 1000 mL.

A sample containing rhI2S (the 26th to 550th amino acids of SEQ ID NO: 10) was desalted by ultrafiltration, and its absorbance at 280 nm was adjusted with water to 0.4 to 0.6. Then 0.2 mL of this desalted sample was dried up under reduced pressure, and then dissolved completely in 0.1 mL of trifluoroacetic acid. The dissolved sample was heated at 100 deg C for 2 hours, then cooled to room temperature, and dried up under reduced pressure. This dried-up sample was dissolved completely in mobile phase A.

Anion exchange chromatography column (Shim-pack ISA-07/52504 (4.0 mm I.D.×250 mm, SHIMAZU) (resin: styrene-divinylbenzene polymer, stationary phase: quaternary ammonium) was connected to SHIMAZU HPLC System LC-Avp (HPLC system for analysis of reducing sugar). The column was set in a column heater (Shim-pack guard column ISA, SHIMAZU) to heat the column at 65 deg C. The flow path from the outlet of the column was connected to a heat block (ALB-221, AGC Techno Glass Co., Ltd.) which was adjusted at 150 deg C. The flow path from the heat block passed through a water bath, and then was connected to a back pressure regulator (U-607, MS Instruments Inc.). Further, the flow path from the back pressure regulator was connected to a fluorescence detector, where the flow was irradiated with excitation light (wavelength: 320 nm) and then fluorescence (wavelength: 430 nm) emitted from the flow was detected. A schematic diagram illustrating the instruments and flow path is given in FIG. 7.

Figure 7:
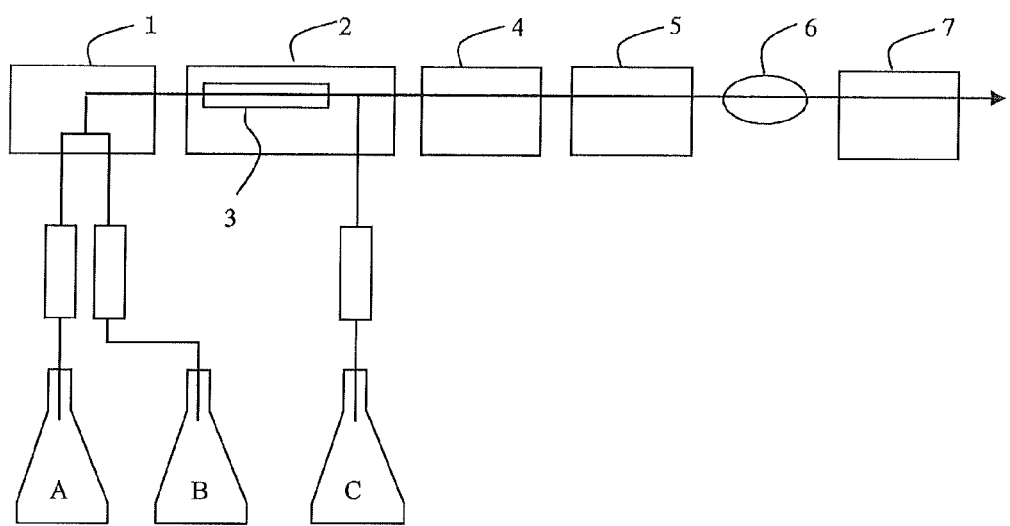
FIG. 7 shows a schematic diagram of the instrument and flow path for measurement of M6P content. 1: autosampler, 2: column heater, 3: column, 4: heat block, 5: water bath, 6: back pressure regulator, 7: fluorescence detector, A: mobile phase A, B: mobile phase B, C: reaction buffer

Containers for mobile phase A and mobile phase B were connected to the autosampler of HPLC system and a container for Reaction buffer was connected to the flow path so that Reaction buffer was supplied between the outlet of the column and the heat block, as illustrated in FIG. 7.

The column was equilibrated with an initial mobile phase (mixture of phase A and mobile phase B at a ration of 40% and 60%, respectively). Twenty microliters of the sample solution or the standard solution was applied to the equilibrated column, and the initial mobile phase was applied for 60 minutes at the flow rate of 0.3 mL/minute. Subsequently, the mobile phase was applied for further 10 minutes at the flow rate of 0.3 mL/minute while, linearly increasing the proportion of mobile phase B from 60% to 100%. The Reaction buffer was constantly applied at the flow rate of 0.2 mL/minute.

The area of the peak detected by the fluorescence detector was calculated, and the amount of mannose-6-phosphate in the sample was determined by comparing the area of the peak obtained, between the sample and the standard solution.

The number of mannose-6-phosphate residues contained per rhI2S (the 26th to 550th amino acids of SEQ ID NO: 10) molecule was calculated by the following formula, where the numbers 282.12 and 77,000 correspond to the molecular weight of mannose-6-phosphate and the approximate molecular weight of rhI2S (the 26th to 550th amino acids of SEQ ID NO: 10) (including linked oligosaccharide chain), respectively.

The number of mannose-6-phosphate per rhI2S (the 26th to 550th amino acids of SEQ ID NO: 10) molecule (mol/mol)) = amount of mannose-6-phosphate in the sample (mg)/amount of rhI2S (the 26th to 550th amino acids of SEQ ID NO: 10) (mg)×282.12/77,000.

The number of M6P residues per molecule of the present rhI2S (the 26th to 550th amino acids of SEQ ID NO: 10) (Lot Nos. 1 to 7) was analyzed to be in the range of 3.74 to 5.38 mol/mol, which averaged to 4.37 mol/mol, whereas the number of M6P residue per molecule of the commercially-available medicinal rhI2S (the 26th to 550th amino acids of SEQ ID NO: 10) was 3.39 mol/mol (See Table 2). The result shows that the present rhI2S (the 26th to 550th amino acids of SEQ ID NO: 10) obtained above method contains a greater number of M6P residues in the oligosaccharide chain linked to it than the commercially-available medicinal rhI2S (the 26th to 550th amino acids of SEQ ID NO: 10), and suggests that this higher M6P content caused the characteristics of the present rhI2S (the 26th to 550th amino acids of SEQ ID NO: 10), including its highly efficient cellular uptake and strong affinity for the M6P receptor.

As the present rhI2S (the 26th to 550th amino acids of SEQ ID NO: 10) have the properties describe above, including highly efficient cellular uptake, it can be more effectively used than the conventional medicament in the enzyme replacement therapy of patients suffering from diseases caused by deficiency of the gene encoding I2S, such as Hunter's syndrome. As it is incorporated efficiently into its target cells, the present rhI2S (the 26th to 550th amino acids of SEQ ID NO: 10), when used as a medicinal enzyme in the enzyme replacement therapy, could lead to substantial reduction of the amount of the enzyme to be injected into a patient. This aspect is very advantageous not only to relating patients and medical facilities but also to the financial aspect of the medical service system, because reduction in the required amount of enzyme in each treatment would eventually result in reduction of the required total production scale of the enzyme, therefore the total cost of its production.

INDUSTRIAL APPLICABILITY

The present invention is utilized for production of recombinant human iduronate 2-sulfatase (rhI2S) (the 26th to 550th amino acids of SEQ ID NO: 10) in a large scale, with a high purity sufficient for its administration to a patient as a medicament, and with attached oligosaccharide chains containing mannose 6-phosphate residues which is necessary for rhI2S (the 26th to 550th amino acids of SEQ ID NO: 10) to be employed in the enzyme replacement therapy for Hunter's syndrome.

[Sequence Listing Free Text]
SEQ ID NO:1=Primer I2S-f
SEQ ID NO:2=Primer I2S-r
SEQ ID NO:3=Primer I2S-f2
SEQ ID NO:4=Primer I2S-r2
SEQ ID NO:5=Synthetic oligonucleotide hGH-f1
SEQ ID NO:6=Synthetic oligonucleotide hGH-r1
SEQ ID NO:7=Synthetic oligonucleotide hGH-f2
SEQ ID NO:8=Synthetic oligonucleotide hGH-r2
SEQ ID NO:9=Human wild-type I2S Amino acid sequence
SEQ ID NO:10=DNA sequence encoding human wild-type I2S
SEQ ID NO:11=Primer hMPR9-f
SEQ ID NO:12=Primer hMPR9-r
SEQ ID NO:13=Synthetic DNA sequence encoding hMPR9 having Bip signal at its N-terminus and His-tag at the C-terminus
SEQ ID NO:14=Primer hMPR9-f2
SEQ ID NO:15=Primer hMPR9-r2
SEQ ID NO:16=Primer hMPR9-f3
SEQ ID NO:17=Primer hMPR9-r3
[Sequence Listing]
GP147-PCT_ST25

The invention claimed is:

1. A method for producing recombinant human wild-type iduronate 2-sulfatase (rhI2S) consisting of the $26^{th}$ to $550^{th}$ amino acids of the amino acid sequence set forth in SEQ ID NO:10, wherein the method comprises:
   (a) culturing rhI2S-producing mammalian cells in a serum-free medium so as to allow the cells to secrete the rhI2S in the medium, wherein the cells are those that have been transformed to express the gene encoding the rhI2S by introduction of the gene using an expression vector in which the gene is incorporated,
   (b) collecting culture supernatant by removing the cells from the culture that is obtained in step (a) above,
   (c) subjecting the culture supernatant collected in step (b) above to cation-exchange column chromatography to collect rhI2S-active fractions,
   (d) subjecting the fractions collected in step (c) above to dye affinity column chromatography to collect rhI2S-active fractions,
   (e) subjecting the fractions collected in step (d) above to anion-exchange column chromatography to collect rhI2S-active fractions,
   (f) subjecting the fractions collected in step (e) above to a column chromatography employing as a solid phase, a material having affinity for phosphate group to collect rhI2S-active fractions, and
   (g) subjecting the fractions collected in step (1) above to gel filtration column chromatography to collect rhI2S-active fractions, in the respective order.

2. The method according to claim 1, wherein the cation exchanger employed in the cation-exchange column chromatography is a weak cation exchanger.

3. The method according to claim 2, wherein the weak cation exchanger has phenyl groups, amide bonds and carboxyl groups.

4. The method according to claim 1, wherein the dye employed in the dye affinity column chromatography is a blue triazine dye.

5. The method according to claim 1, wherein the material having affinity for phosphate group is selected from the group consisting of fluoroapatite and hydroxyapatite.

6. The method according to claim 5, wherein the material having affinity to phosphate group is fluoroapatite.

7. The method according to claim 1, wherein the mammalian cells are CHO cells transfected with an expression vector which is designed to express rhI2S under the regulation of EF-1(alpha) promoter.

8. A method for purifying recombinant human wild-type iduronate 2-sulfatase (rhI2S) consisting of the $26^{th}$ to $550^{th}$ amino acids of the amino acid sequence set forth in SEQ ID NO:10 from contaminants in a sample, wherein the rhI2S has an oligosaccharide chain linked thereto containing one or more mannose 6-phosphate residues, the method comprising:
   (a) applying the sample to a chromatography column which employs fluoroapatite as a solid phase,
   (b) flowing a first mobile phase through the column to wash the column while letting the rhI2S be adsorbed by the column, and
   (c) eluting the rhI2S from the column by flowing a second mobile phase through the column, wherein the second mobile phase contains a phosphate at a higher concentration than the first mobile phase.

* * * * *